United States Patent
Kim et al.

(10) Patent No.: US 9,012,039 B2
(45) Date of Patent: Apr. 21, 2015

(54) COMPOUND FOR ORGANIC PHOTOELECTRIC DEVICE AND ORGANIC PHOTOELECTRIC DEVICE INCLUDING THE SAME

(75) Inventors: Nam-Soo Kim, Uiwang-si (KR);
Myeong-Soon Kang, Uiwang-si (KR);
Sung-Hyun Jung, Uiwang-si (KR);
Ho-Kuk Jung, Uiwang-si (KR);
Kyu-Yeol In, Uiwang-si (KR);
Dong-Min Kang, Uiwang-si (KR);
Eui-Su Kang, Uiwang-si (KR);
Nam-Heon Lee, Uiwang-si (KR);
Seung-Gyoung Lee, Uiwang-si (KR);
Young-Sung Park, Uiwang-si (KR);
Hyon-Gyu Lee, Uiwang-si (KR);
Eun-Sun Yu, Uiwang-si (KR);
Mi-Young Chae, Uiwang-si (KR)

(73) Assignee: Cheil Industries, Inc., Gumi-si, Gyeongsangbuk-do (KR)

( * ) Notice: Subject to any disclaimer, the term of this patent is extended or adjusted under 35 U.S.C. 154(b) by 136 days.

(21) Appl. No.: 12/979,869

(22) Filed: Dec. 28, 2010

(65) Prior Publication Data
US 2011/0156013 A1    Jun. 30, 2011

(30) Foreign Application Priority Data
Dec. 29, 2009    (KR) .................. 10-2009-0133225

(51) Int. Cl.
*H01L 51/54*    (2006.01)
*C07D 251/12*    (2006.01)
*C07D 401/10*    (2006.01)
*H01L 51/00*    (2006.01)
(Continued)

(52) U.S. Cl.
CPC .......... *C07D 401/10* (2013.01); *H01L 51/0067* (2013.01); *H01L 51/0072* (2013.01); *H01L 51/0081* (2013.01); *H01L 51/5012* (2013.01); *C09B 57/00* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 7,612,500 B2* | 11/2009 | Sotoyama | 313/506 |
| 7,749,617 B2 | 7/2010 | Suzuki et al. | |
| 2007/0051944 A1* | 3/2007 | Vestweber et al. | 257/40 |

(Continued)

FOREIGN PATENT DOCUMENTS

| | | | | |
|---|---|---|---|---|
| JP | 2003045662 A | * | 2/2003 | ............. H05B 33/22 |
| JP | 2006-076901 A | | 3/2006 | |

(Continued)

OTHER PUBLICATIONS

Machine English translation of JP 2003-045662 A. Apr. 1, 2012.*

(Continued)

*Primary Examiner* — J. L. Yang
(74) *Attorney, Agent, or Firm* — Lee & Morse, P.C.

(57) ABSTRACT

A compound for an organic photoelectric device and an organic photoelectric device including the same, the compound being represented by the following Chemical Formula 1:

[Chemical Formula 1]

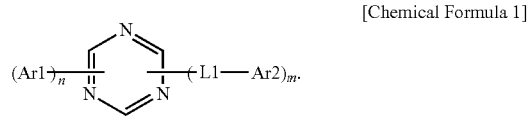

12 Claims, 3 Drawing Sheets

(51) Int. Cl.
*C09B 57/00* (2006.01)
*H01L 51/50* (2006.01)

(56) References Cited

U.S. PATENT DOCUMENTS

2009/0281311 A1    11/2009   Yamakawa et al.
2010/0044695 A1     2/2010   Kai et al.
2011/0284832 A1*   11/2011   In et al. ............... 257/40

FOREIGN PATENT DOCUMENTS

| | | |
|---|---|---|
| JP | 2007-137829 A | 6/2007 |
| KR | 10 2008-0016007 A | 2/2008 |
| KR | 10 2008-0039941 A | 5/2008 |
| KR | 10 2009-0131958 A | 12/2009 |
| KR | 10 2010-0015581 A | 2/2010 |
| KR | 10 2010-0024340 A | 3/2010 |
| KR | 10 2010-0075358 A | 7/2010 |
| WO | WO 2010/024572 A2 | 3/2010 |
| WO | WO 2010/074422 A1 | 7/2010 |

OTHER PUBLICATIONS

English translation of JP 2003-045662 A. Mar. 2, 2014.*
Machine English translation of Kido et al. (JP 2007-137829 A). Dec. 17, 2013.*
Tang, et al.; Organic electroluminescent diodes; Applied Physics Letters; Sep. 21, 1987; 913-915; vol. 51, Issue 12; American Institute of Physics; United States.
O'Brien, et al.; Improved energy transfer in electrophosphorescent devices; Applied Physics Letters; Jan. 18, 1999, pp. 442-444; vol. 74, No. 3; American Institute of Physics, United States.
Baldo, et al.; Very high-efficiency green organic light-emitting devices based on eletrophosphorescence; Applied Physics Letters; Jul. 5, 1999; pp. 4-6; vol. 75, No. 1; American Institute of Physics; United States.

* cited by examiner

COMPOUND FOR ORGANIC PHOTOELECTRIC DEVICE AND ORGANIC PHOTOELECTRIC DEVICE INCLUDING THE SAME

BACKGROUND

1. Field

Embodiments relate to a compound for an organic photoelectric device and an organic photoelectric device including the same.

2. Description of the Related Art

A photoelectric device may be, in a broad sense, a device for transforming photo-energy to electrical energy, or conversely, a device for transforming electrical energy to photo-energy.

An organic photoelectric device may be classified as follows in accordance with its driving principles. One type of organic photoelectric device may be an electron device driven as follows: excitons may be generated in an organic material layer in response to photons from an external light source; the excitons may be separated into electrons and holes; and the electrons and holes may be transferred to different electrodes as a current source (voltage source).

Another type of organic photoelectric device may be an electron device driven as follows: a voltage or a current may be applied to at least two electrodes to inject holes and/or electrons into an organic material semiconductor positioned at an interface of the electrodes; and the device may be driven by the injected electrons and holes.

SUMMARY

Embodiments are directed to a compound for an organic photoelectric device and an organic photoelectric device including the same.

The embodiments may be realized by providing a compound for an organic photoelectric device represented by the following Chemical Formula 1:

[Chemical Formula 1]

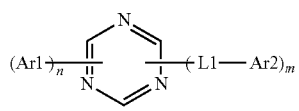

wherein, in Chemical Formula 1, Ar1 is a substituted or unsubstituted C10 to C30 fused aryl group, Ar2 is a substituted or unsubstituted quinolinyl group or a substituted or unsubstituted isoquinolinyl group, L1 is a substituted or unsubstituted C6 to C20 arylene group, and n and m are integers of 1 or 2, m+n being 3.

Ar1 may be selected from a substituted or unsubstituted naphthyl group, a substituted or unsubstituted naphthylphenyl group, a substituted or unsubstituted phenanthrenyl group, a substituted or unsubstituted anthracenyl group, and a substituted or unsubstituted pyrenyl group.

Ar2 may be a substituted or unsubstituted quinolinyl group.

L1 may be linked to Ar2 at a number 4 or 8 position of the substituted or unsubstituted quinolinyl group thereof.

L1 may be selected from a substituted or unsubstituted phenylene, a substituted or unsubstituted biphenylene, and a substituted or unsubstituted naphthylene.

The embodiments may also be realized by providing a compound for an organic photoelectric device represented by the following Chemical Formula 2:

[Chemical Formula 2]

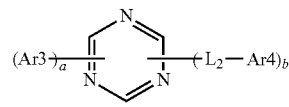

wherein, in Chemical Formula 2, Ar3 is a substituted or unsubstituted C6 to C30 aryl group, Ar4 is a substituted or unsubstituted quinolinyl group, L2 is a substituted or unsubstituted C6 to C20 arylene group, and a and b are integers of 1 or 2, a+b being 3.

Ar3 may be selected from a substituted or unsubstituted phenyl group, a substituted or unsubstituted biphenyl group, a substituted or unsubstituted naphthyl group, a substituted or unsubstituted naphthylphenyl group, a substituted or unsubstituted phenanthrenyl group, a substituted or unsubstituted anthracenyl group, and a substituted or unsubstituted pyrenyl group.

L2 may be linked to Ar4 at a number 4 or 8 position of the substituted or unsubstituted quinolinyl group thereof.

L2 may be selected from a substituted or unsubstituted phenylene, a substituted or unsubstituted biphenylene, and a substituted or unsubstituted naphthylene.

The embodiments may also be realized by providing a compound for an organic photoelectric device represented by the one of the following Chemical Formulae 3 to 8:

[Chemical Formula 3]

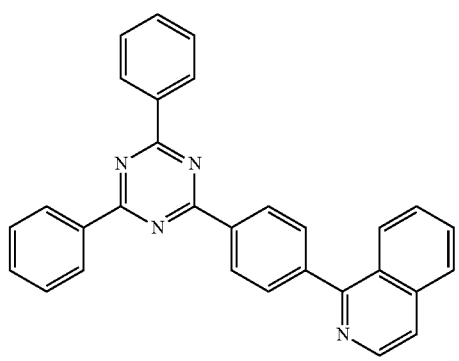

[Chemical Formula 4]

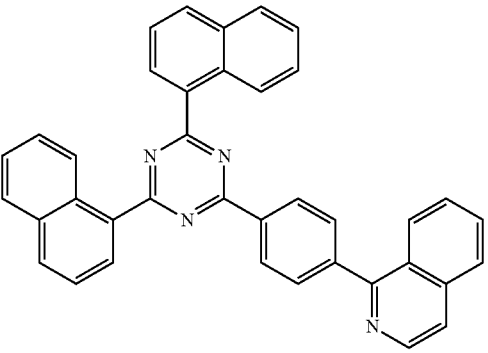

[Chemical Formula 5]
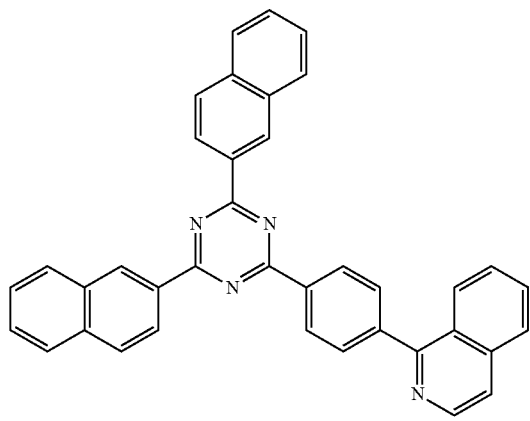
[Chemical Formula 6]
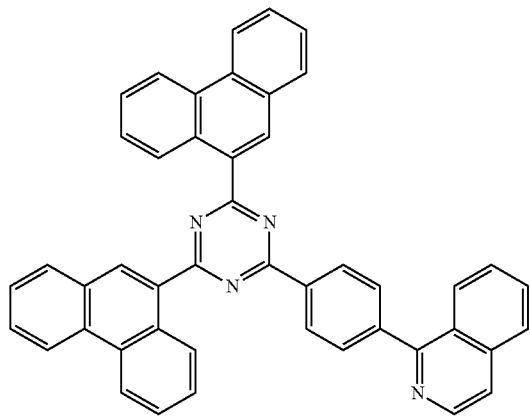
[Chemical Formula 7]
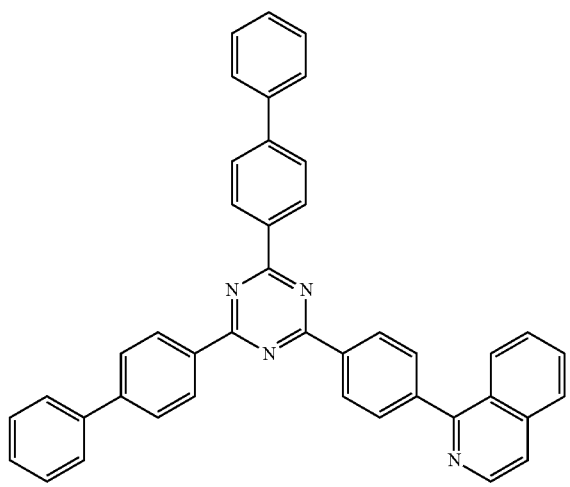
[Chemical Formula 8]
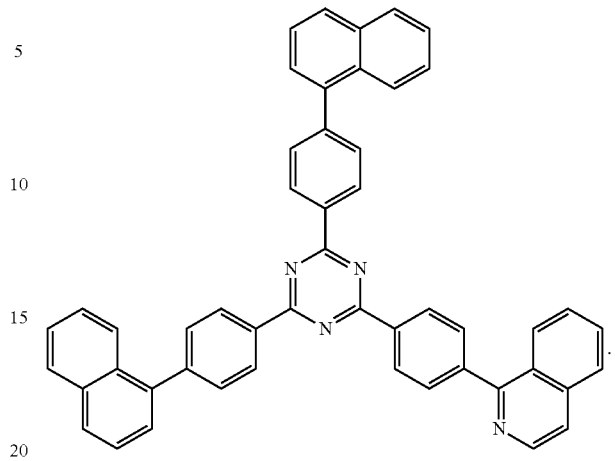
The embodiments may also be realized by providing a compound for an organic photoelectric device represented by the one of the following Chemical Formulae 9 to 26:
[Chemical Formula 9]
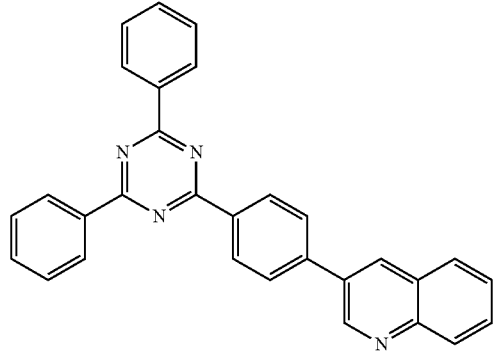
[Chemical Formula 10]
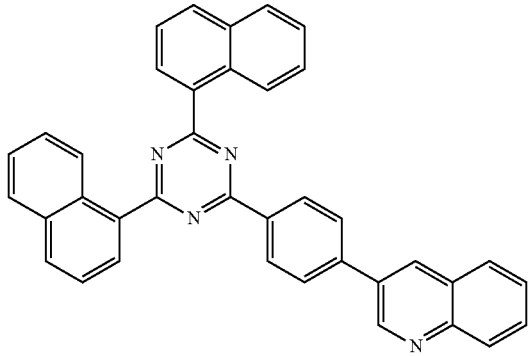

[Chemical Formula 11]
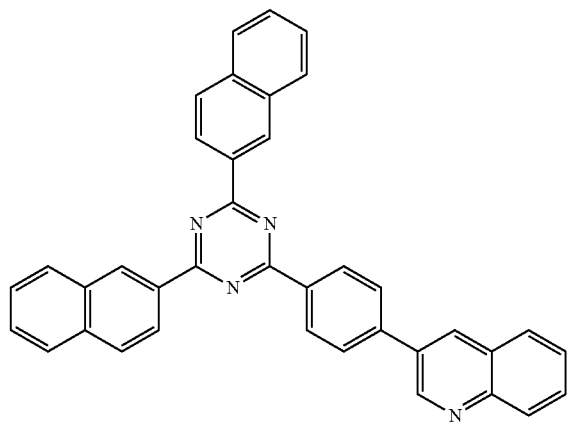
[Chemical Formula 12]
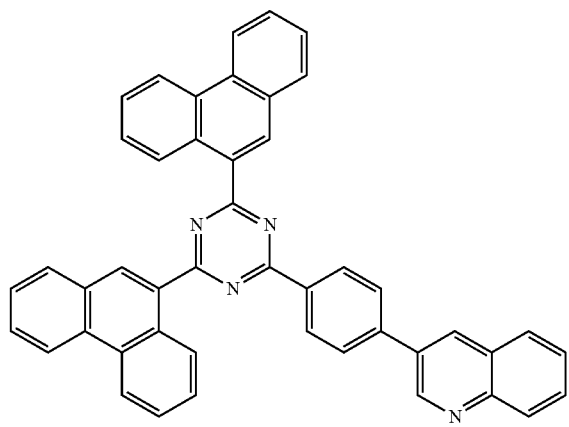
[Chemical Formula 13]
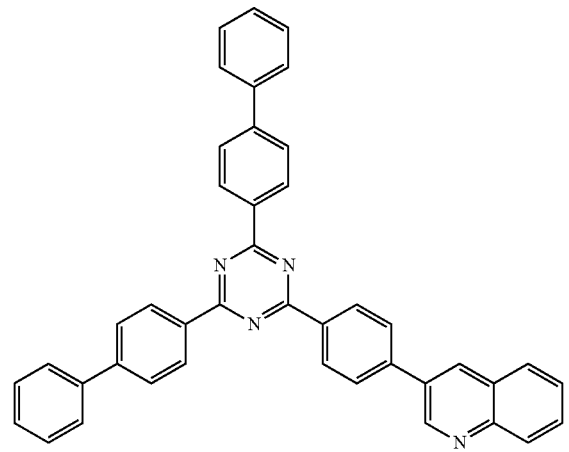
[Chemical Formula 14]
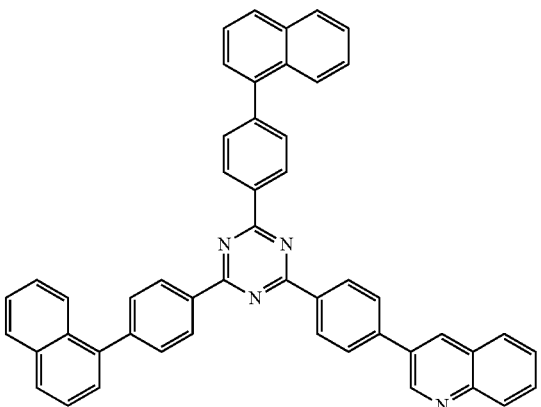
[Chemical Formula 15]
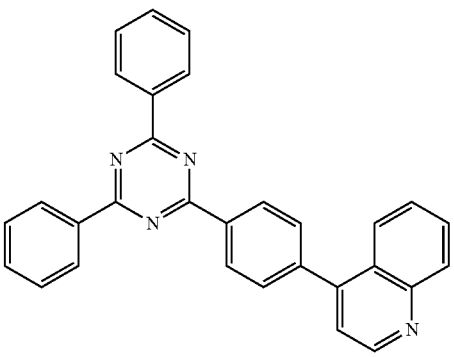
[Chemical Formula 16]
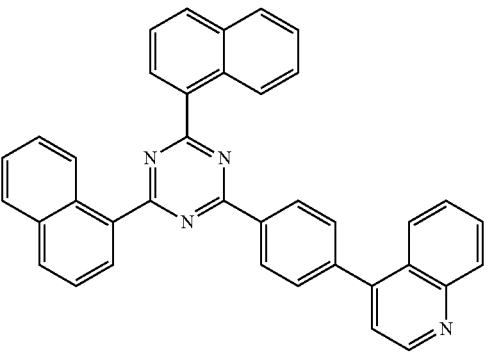
[Chemical Formula 17]
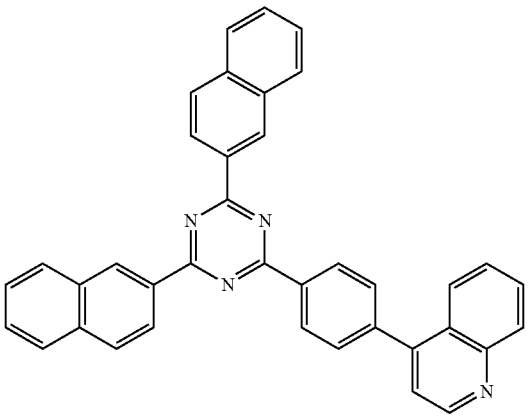

[Chemical Formula 18]
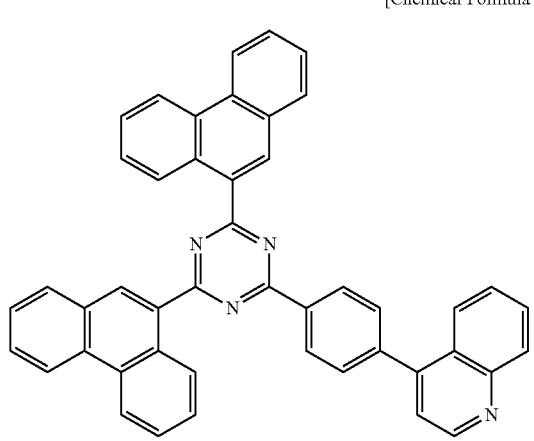
[Chemical Formula 19]
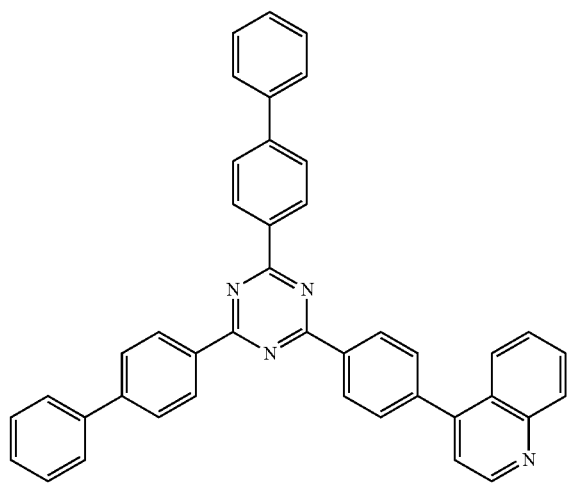
[Chemical Formula 20]
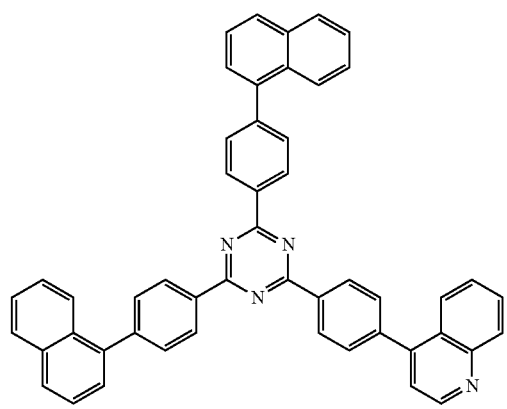
[Chemical Formula 21]
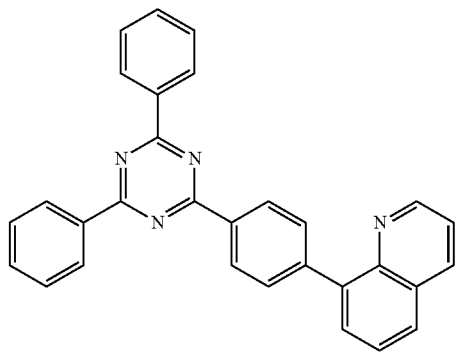
[Chemical Formula 22]
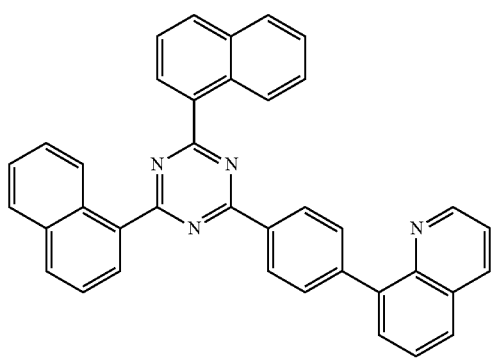
[Chemical Formula 23]
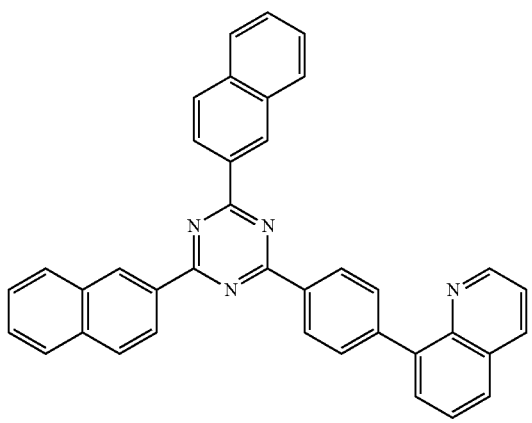
[Chemical Formula 24]
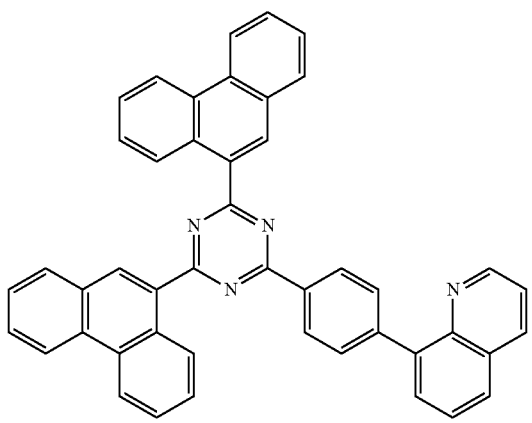

[Chemical Formula 25]
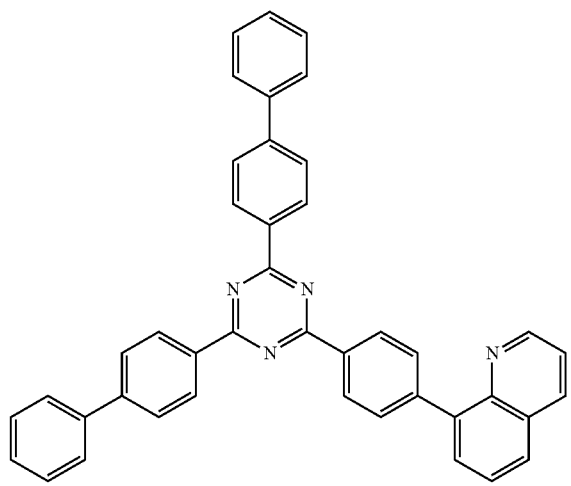
[Chemical Formula 28]
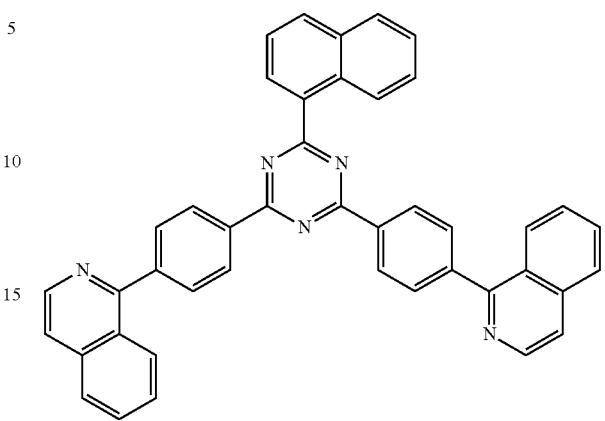
[Chemical Formula 26]
[Chemical Formula 29]
The embodiments may also be realized by providing a compound for an organic photoelectric device represented by the one of the following Chemical Formulae 27 to 32:
[Chemical Formula 27]
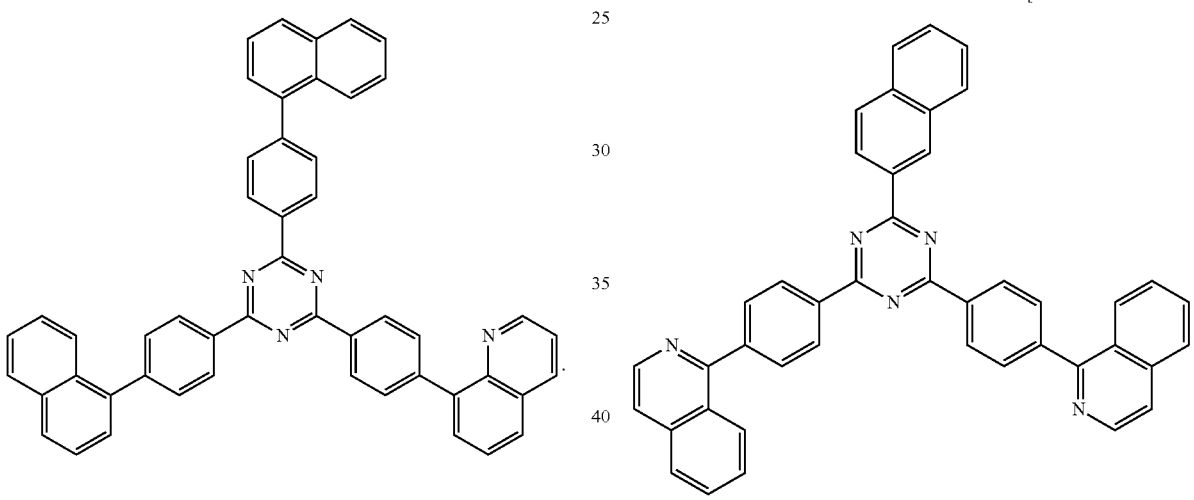
[Chemical Formula 30]
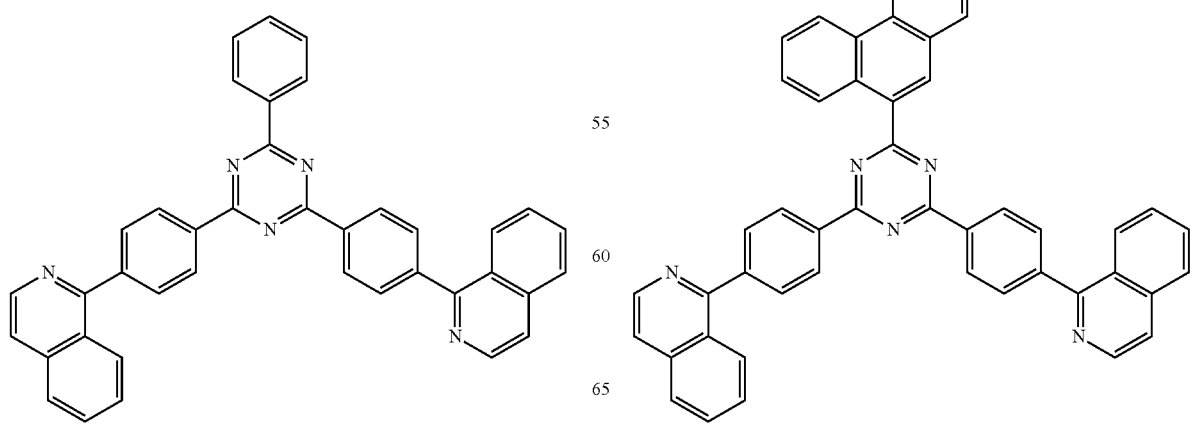

[Chemical Formula 31]
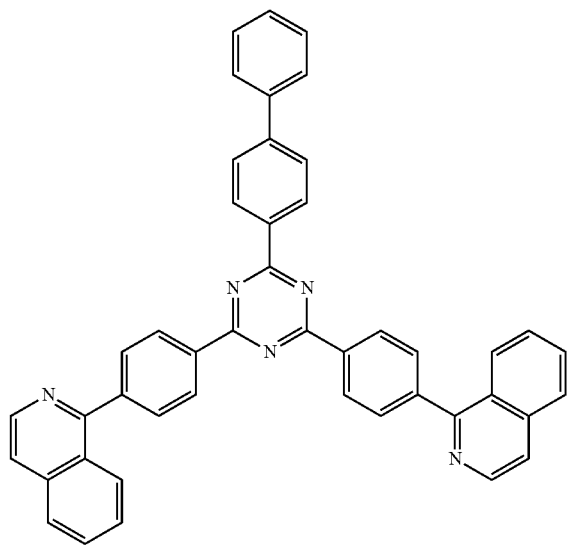
[Chemical Formula 32]
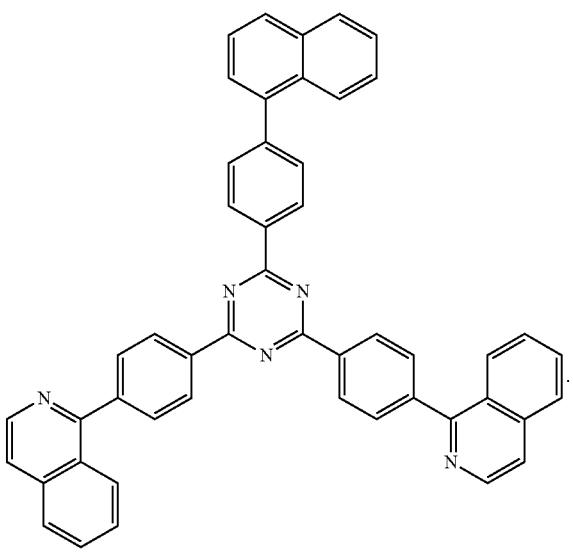
The embodiments may also be realized by providing a compound for an organic photoelectric device represented by the one of the following Chemical Formulae 33 to 50:
[Chemical Formula 33]
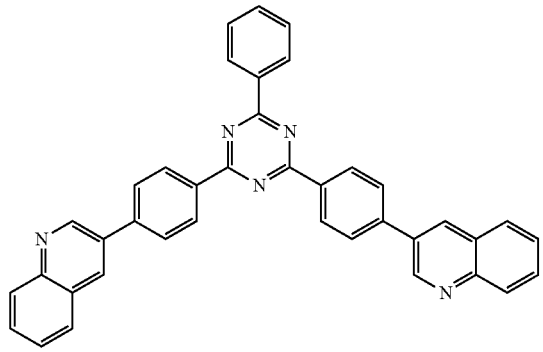
[Chemical Formula 34]
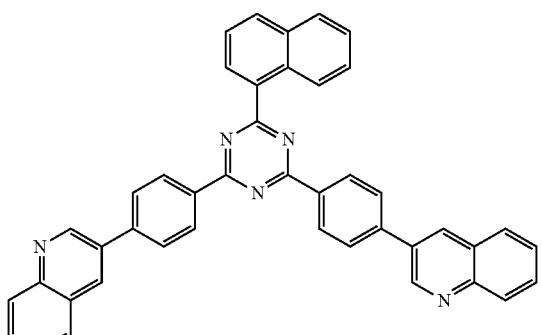
[Chemical Formula 35]
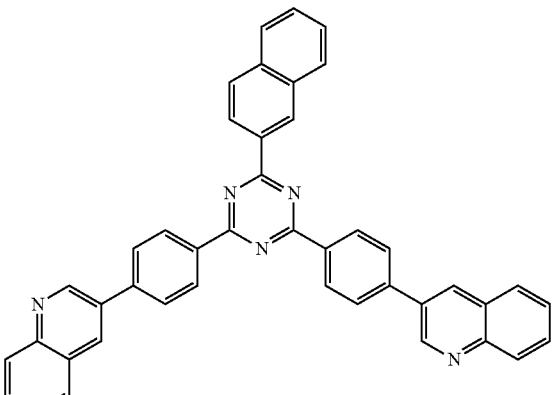
[Chemical Formula 36]
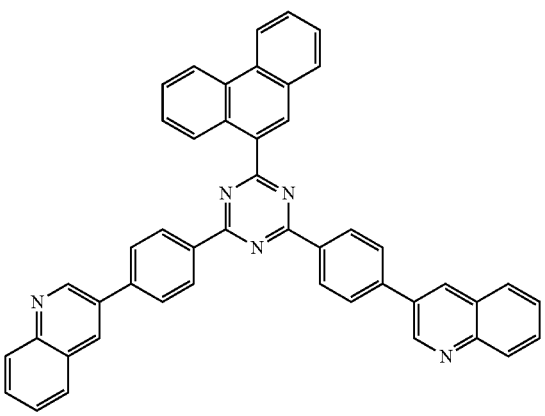

[Chemical Formula 37]
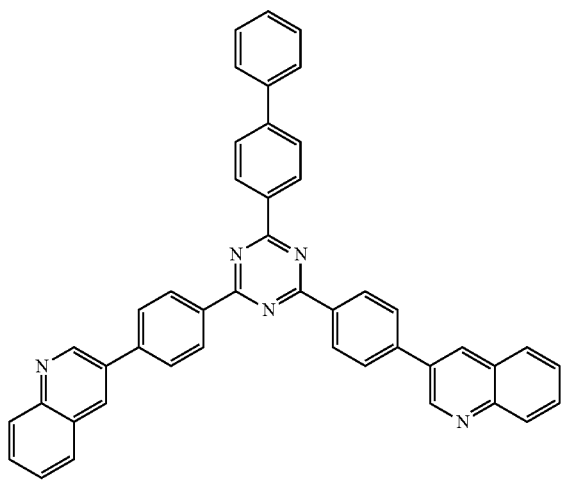
[Chemical Formula 38]
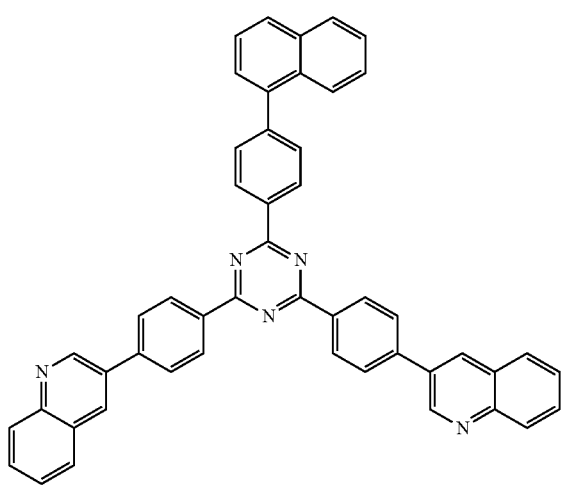
[Chemical Formula 39]
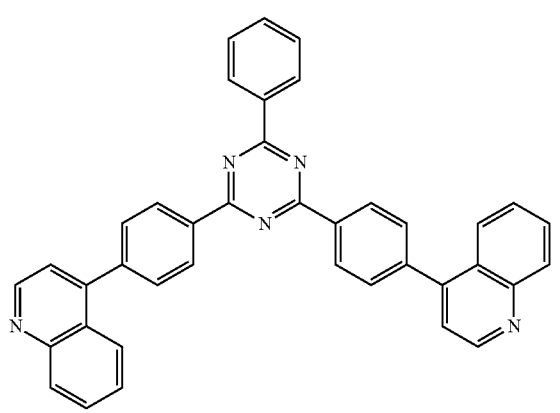
[Chemical Formula 40]
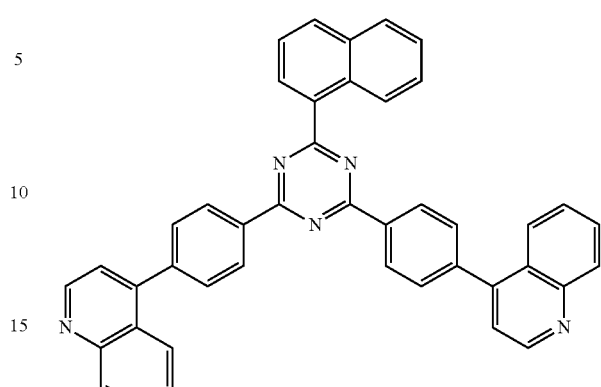
[Chemical Formula 41]
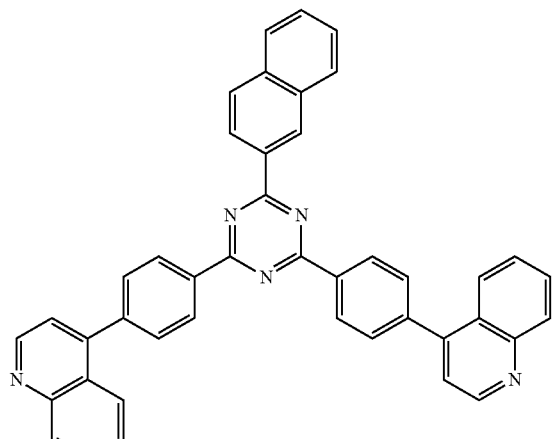
[Chemical Formula 42]
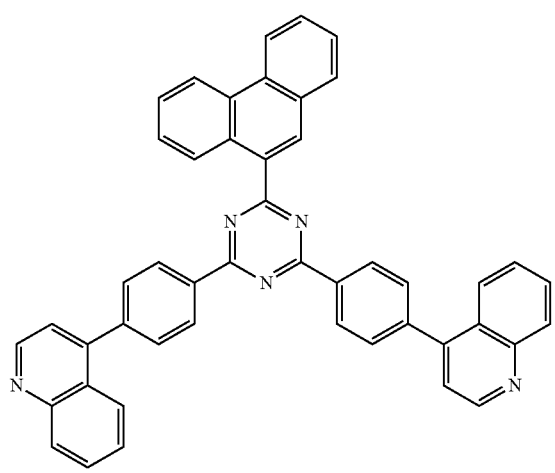

[Chemical Formula 43]
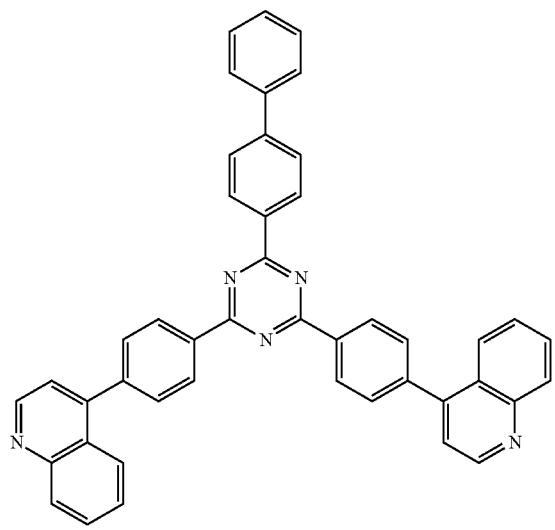
[Chemical Formula 44]
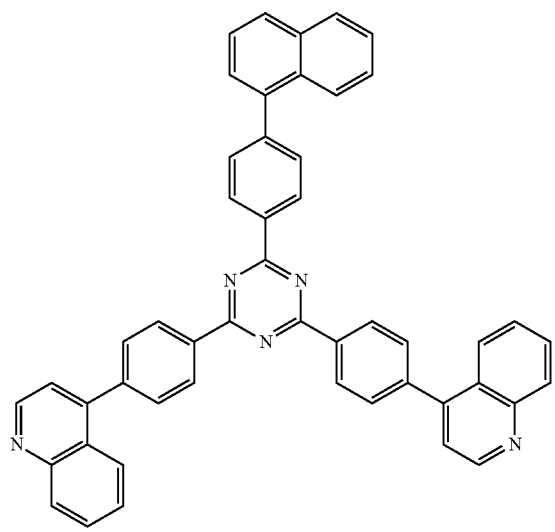
[Chemical Formula 45]
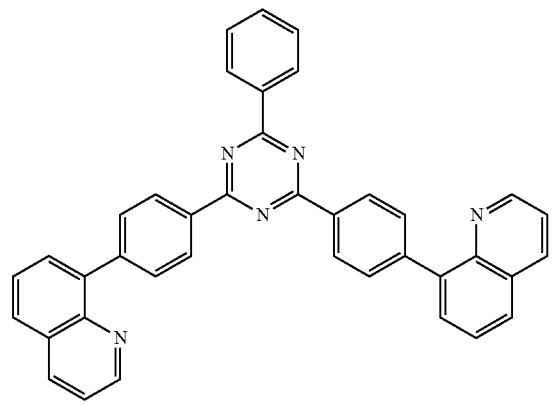
[Chemical Formula 46]
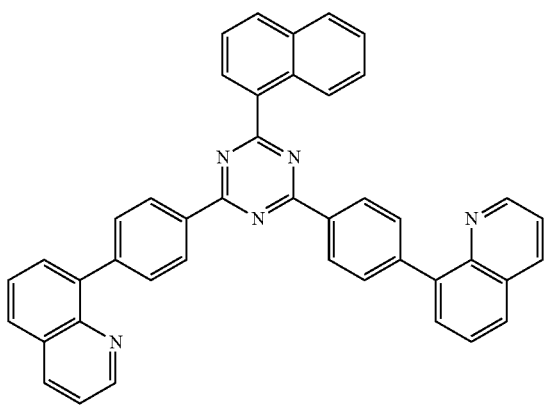
[Chemical Formula 47]
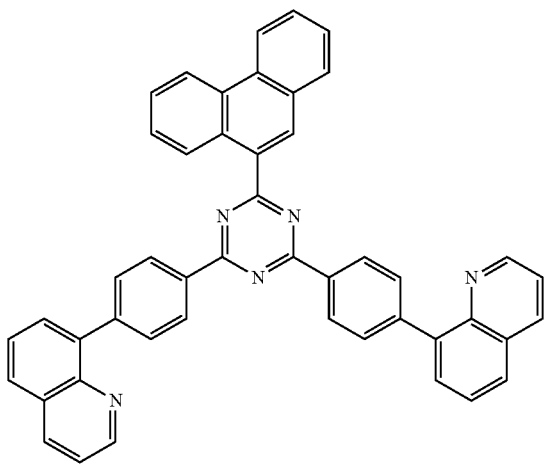
[Chemical Formula 48]

17
-continued

[Chemical Formula 49]

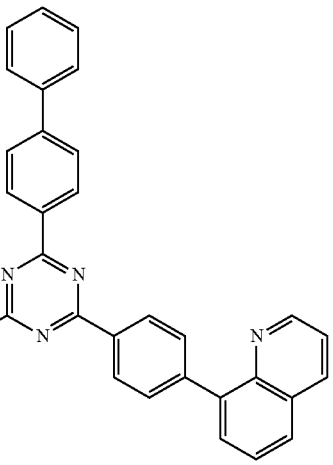

[Chemical Formula 50]

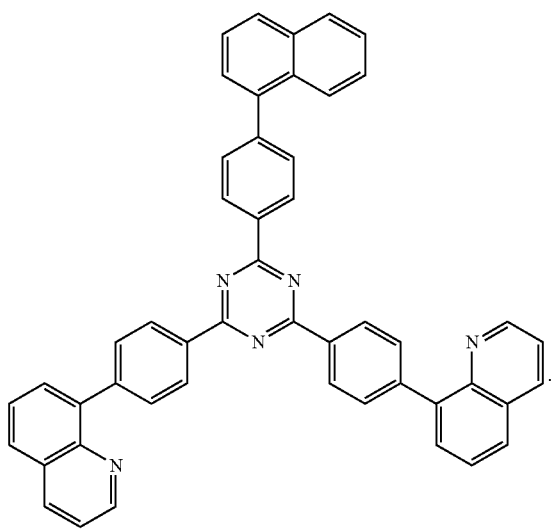

The embodiments may also be realized by providing an organic photoelectric device including an anode; a cathode, and one or more organic thin layers between the anode and cathode, wherein at least one of the organic thin layers includes the compound for an organic photoelectric device according to an embodiment.

The one or more organic thin layers may include at least one of an emission layer, a hole transport layer (HTL), a hole injection layer (HIL), an electron transport layer (ETL), an electron injection layer (EIL), and a hole blocking layer.

The at least one organic thin layer may include at least one of an electron transport layer (ETL) and an electron injection layer (EIL), the compound for the organic photoelectric device being included in the electron transport layer (ETL) or the electron injection layer (EIL).

The at least one organic thin layer may include an emission layer, the compound for the organic photoelectric device being included in the emission layer.

The at least one organic thin layer may include an emission layer, the compound for the organic photoelectric device being a phosphorescent or fluorescent host material in the emission layer.

18

The at least one organic thin layer may include an emission layer, the compound for the organic photoelectric device being a fluorescent blue dopant material in the emission layer.

The organic photoelectric device may be an organic light emitting device, an organic solar cell, an organic transistor, an organic photo-conductor drum, or an organic memory device.

BRIEF DESCRIPTION OF THE DRAWINGS

The embodiments will become more apparent to those of ordinary skill in the art by describing in detail exemplary embodiments with reference to the attached drawings, in which.

DETAILED DESCRIPTION

Figure 1:
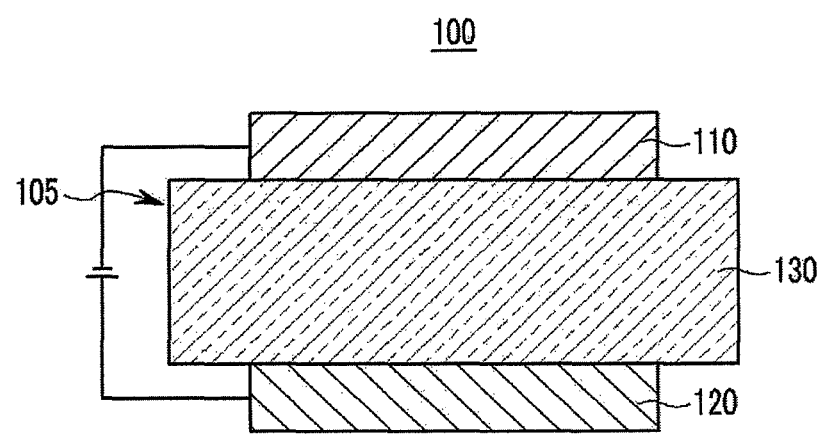
FIGS. 1 to 5 illustrate cross-sectional views of organic light emitting diodes including compounds according to various embodiments.

Korean Patent Application No. 10-2010-0133225, filed on Dec. 29, 2009, in the Korean Intellectual Property Office, and entitled: "Compound for Organic Photoelectric Device and Organic Photoelectric Device Including the Same," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, the term "substituted" may refer to one substituted with a C1 to C30 an alkyl group, a C1 to C10 alkylsilyl group, a C3 to C30 cycloalkyl group, a C6 to C30 aryl group, a C1 to C10 alkoxy group, a fluoro group, a C1 to C10 trifluoroalkyl group such as a trifluoromethyl group, or a cyano group.

As used herein, when specific definition is not otherwise provided, the term "hetero" may refer to one including 1 to 3 of N, O, S, or P, and remaining carbons in one ring.

As used herein, when a definition is not otherwise provided, the term "combination thereof" may refer to at least two substituents bound to each other by a linker, or at least two substituents condensed to each other.

As used herein, when a definition is not otherwise provided, the term "alkyl" may refer to an aliphatic hydrocarbon group. The alkyl may be a saturated alkyl group that does not include any alkene or alkyne. Alternatively, the alkyl may be an unsaturated alkyl group that includes at least one alkene or alkyne. The term "alkene" may refer to a group in which at least two carbon atoms are bound in at least one carbon-carbon double bond, and the term "alkyne" may refer to a group in which at least two carbon atoms are bound in at least one carbon-carbon triple bond. Regardless of being saturated or unsaturated, the alkyl may be branched, linear, or cyclic.

The alkyl group may have 1 to 20 carbon atoms. The alkyl group may be a medium-sized alkyl having 1 to 10 carbon atoms. The alkyl group may be a lower alkyl having 1 to 6 carbon atoms.

For example, a C1-C4 alkyl may have 1 to 4 carbon atoms and may be selected from the group of methyl, ethyl, propyl, iso-propyl, n-butyl, iso-butyl, sec-butyl, and t-butyl.

Examples of an alkyl group may be selected from the group of methyl, ethyl, propyl, isopropyl, butyl, isobutyl, t-butyl, pentyl, hexyl, ethenyl, propenyl, butenyl, cyclopropyl, cyclobutyl, cyclopentyl, cyclohexyl, or the like, which may be individually and independently substituted.

The term "aryl" may refer to an aryl group including a carbocyclic aryl (e.g., phenyl) having at least one ring having a covalent or conjugated pi electron system. The term also refers to monocyclic or fused ring polycyclic (i.e., rings sharing adjacent pairs of carbon atoms) groups. In addition, this term may also refer to a spiro compound having a contact point of one carbon.

The compound for an organic photoelectric device according to an embodiment may have a structure in which an aryl group and a heteroaryl group are bound to a core of triazine.

In addition, the compound for an organic photoelectric device according to an embodiment may be formed by synthesis of a compound having various energy band gaps by introducing various substituents into the core of triazine, thus forming a compound satisfying conditions desirable for the emission layer, the electron injection layer (EIL), and/or electron transport layer (ETL).

The organic photoelectric device may include the compound having the appropriate energy level depending upon the substituents. Thus, electron transporting properties and hole inhibition properties may be enhanced to thereby provide excellent efficiency and driving voltage. Electrochemical and thermal stabilities may be improved to thereby enhance life span characteristics during driving the organic photoelectric device.

According to an embodiment, a compound for an organic photoelectric device may be represented by the following Chemical Formula 1.

[Chemical Formula 1]

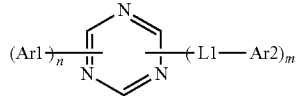

In Chemical Formula 1, Ar1 may be a substituted or unsubstituted C10 to C30 fused aryl group. Examples of Ar1 may include a substituted or unsubstituted naphthyl group, a substituted or unsubstituted naphthylphenyl group, a substituted or unsubstituted phenanthrenyl group, a substituted or unsubstituted anthracenyl group, or a substituted or unsubstituted pyrenyl group. In an implementation, each Ar1 may independently include, e.g., a substituted or unsubstituted naphthyl group, a substituted or unsubstituted naphthylphenyl group, a substituted or unsubstituted phenanthrenyl group, a substituted or unsubstituted anthracenyl group, or a substituted or unsubstituted pyrenyl group.

The triazine core structure to which the aryl group, Ar1 and/or Ar2 is combined or bonded may exhibit excellent thermal safety or oxidation resistance and may improve the life span of an organic photoelectric device.

Ar2 may be a substituted or unsubstituted quinolinyl group or a substituted or unsubstituted isoquinolinyl group, quinoline and isoquinoline being illustrated below. In an implementation, each Ar2 may independently include, e.g., a substituted or unsubstituted quinolinyl group or a substituted or unsubstituted isoquinolinyl group.

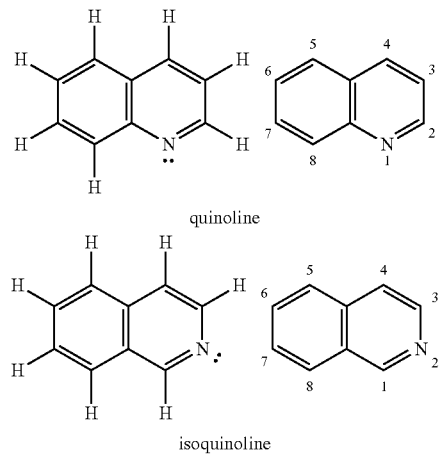

quinoline isoquinoline

When the triazine core structure is substituted with an n-type heteroaryl group having electron affinity, e.g., a quinolinyl group and/or an isoquinolinyl group, an n-type compound having excellent electron transport capability may be provided.

The n-type property means a property of a conductive characteristic depending upon the LUMO level, so as to have an anionic characteristic due to electron formation. Such a triazine core structure with which the heteroaryl group is combined may exhibit enhanced electron transport capability and may exhibit improved efficiency and driving voltage of a device. Thus, an electron injection layer (EIL) or electron transport layer (ETL) material may be usefully used.

For example, Ar2 may be a substituted or unsubstituted quinolinyl group; and L1 may be linked or bonded to Ar2 at a number 4 or 8 position of Ar2, e.g., the 4 or 8 position of the substituted or unsubstituted quinolinyl group. In order to control the above-described properties, the linking or bonding positions may be adjusted.

L1 may be a substituted or unsubstituted C6 to C20 arylene group. Examples of L1 may include a substituted or unsubstituted phenylene, a substituted or unsubstituted biphenylene, or a substituted or unsubstituted naphthylene. In an implementation, each L1 may independently include, e.g., a substituted or unsubstituted C6 to C20 arylene group.

Light emission may be controlled in the visible region by adjusting a π-conjugation length of L1. Accordingly, the compound may be usefully applied to the emission layer of an organic photoelectric device. Maintaining a carbon number of the L1 group at about 20 or less may provide obtain sufficient effects for the device.

n and m may be integers of 1 or 2, and m+n may be equal to 3. In order to control the above-described properties, the numbers of substituents may be adjusted.

The compound of Chemical Formula 1 may include the core part of triazine and the parts of Ar1, Ar2, and L1. The triazine may exhibit relatively high thermal stability or oxidation resistance, and may have various substituents at 1, 3, and 5 positions by controlling a ratio of reactants.

Another embodiment provides a compound for an organic photoelectric device represented by the following Chemical Formula 2.

[Chemical Formula 2]

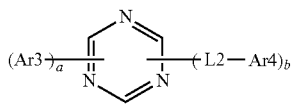

In Chemical Formula 2, Ar3 may be a substituted or unsubstituted C6 to C30 aryl group. Examples of Ar3 may include a substituted or unsubstituted phenyl group, a substituted or unsubstituted biphenyl group, a substituted or unsubstituted naphthyl group, a substituted or unsubstituted naphthylphenyl group, a substituted or unsubstituted phenanthrenyl group, a substituted or unsubstituted anthracenyl group, or a substituted or unsubstituted pyrenyl group. In an implementation, each Ar3 may independently include, e.g., a substituted or unsubstituted phenyl group, a substituted or unsubstituted biphenyl group, a substituted or unsubstituted naphthyl group, a substituted or unsubstituted naphthylphenyl group, a substituted or unsubstituted phenanthrenyl group, a substituted or unsubstituted anthracenyl group, or a substituted or unsubstituted pyrenyl group.

The triazine core structure to which the aryl groups, e.g., Ar3 and Ar4, are combined or bonded may exhibit excellent thermal safety or oxidation resistance and may improve the life span of an organic photoelectric device.

Ar4 may be a substituted or unsubstituted quinolinyl group. In an implementation, each Ar4 may independently include a substituted or unsubstituted quinolinyl group, quinoline being illustrated below.

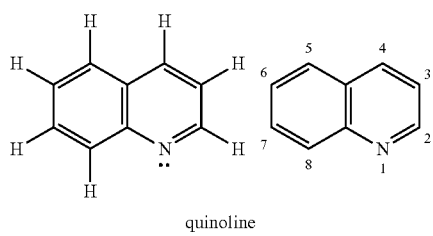

quinoline

When the triazine core structure is substituted with an n-type heteroaryl group having electron affinity, e.g., a quinolinyl group, an n-type compound having excellent electron transport capability may be provided.

L2 may be linked to Ar4 at a number 4 or 8 position of Ar4, e.g., at a number 4 or 8 position of the quinolinyl group. In order to control the above-described properties, the linking positions may be adjusted.

L2 may be a substituted or unsubstituted C6 to C20 arylene group. Examples of L2 may include a substituted or unsubstituted phenylene, a substituted or unsubstituted biphenylene, or a substituted or unsubstituted naphthylene. In an implementation, each L2 may independently include, e.g., a substituted or unsubstituted C6 to C20 arylene group.

Light emission may be controlled in the visible region by adjusting the π-conjugation length of L2. Accordingly, the compound may be usefully applied to the emission layer of an organic photoelectric device. Maintaining a carbon number of the L2 group at about 20 or less may help ensure that it is possible to obtain sufficient effects for the device.

In Chemical Formula 2, a and b may be integers of 1 or 2, and a+b may be 3. In order to control the above-described properties, the numbers of substituents may be adjusted.

As described above, the compound of Chemical Formula 2 according to an embodiment may include the core part of triazine and the parts of Ar3, Ar4, and L2. The triazine may exhibit relatively high thermal stability or oxidation resistance and may include various substituents at 1, 3, and 5 positions by controlling a ratio of reactants.

The compound for an organic photoelectric device represented by the above Chemical Formulae 1 or 2 may include compounds represented by the following Chemical Formulae 3 to 50. However, the compounds are not limited thereto.

[Chemical Formula 3]

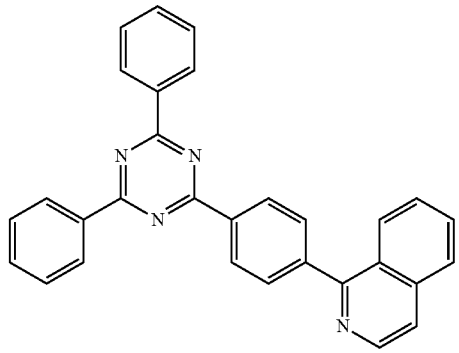

[Chemical Formula 4]

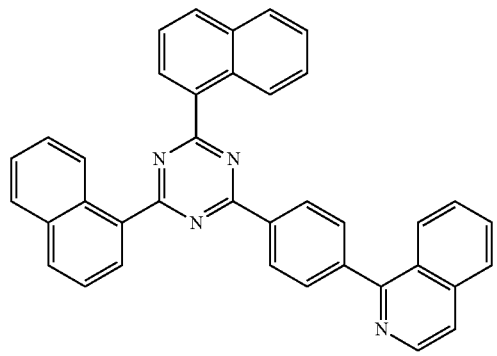

[Chemical Formula 5]

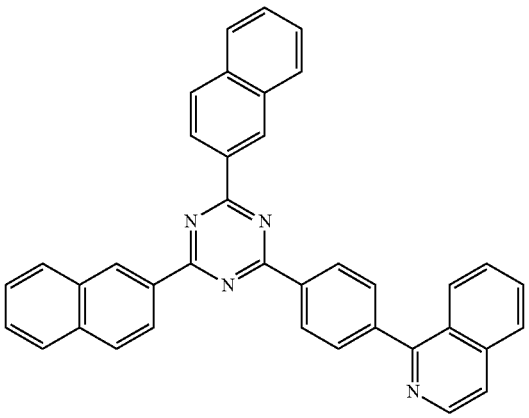

[Chemical Formula 6]
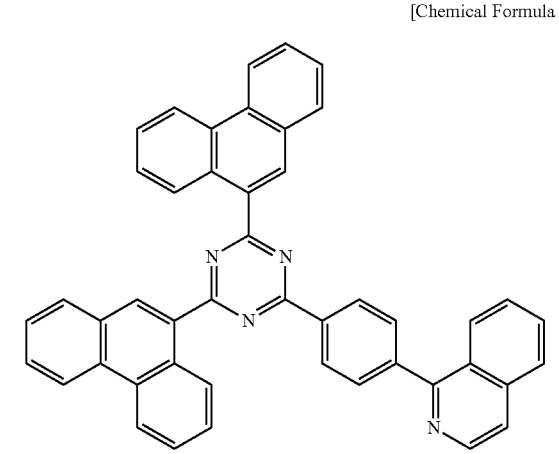
[Chemical Formula 7]
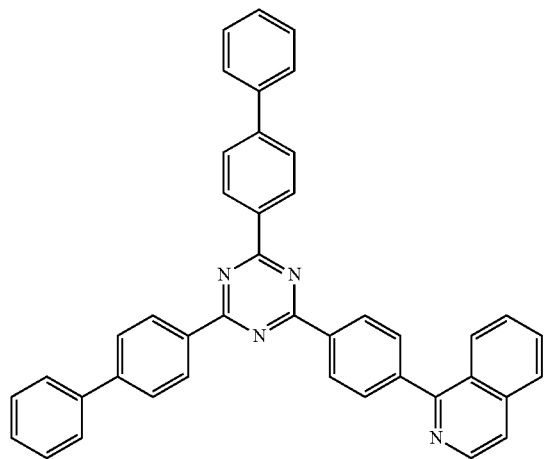
[Chemical Formula 8]
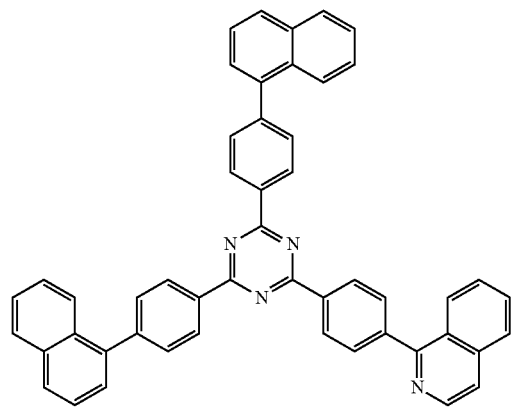
[Chemical Formula 9]
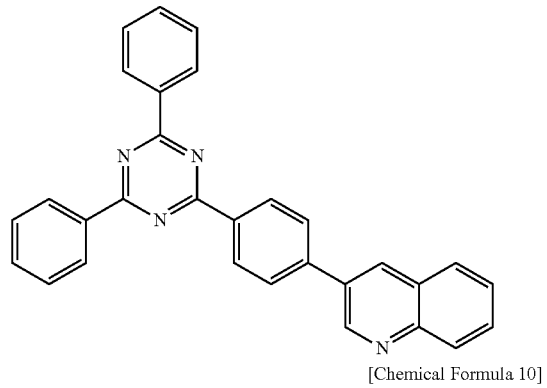
[Chemical Formula 10]
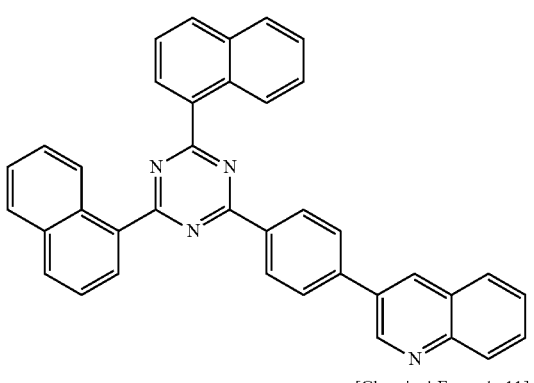
[Chemical Formula 11]
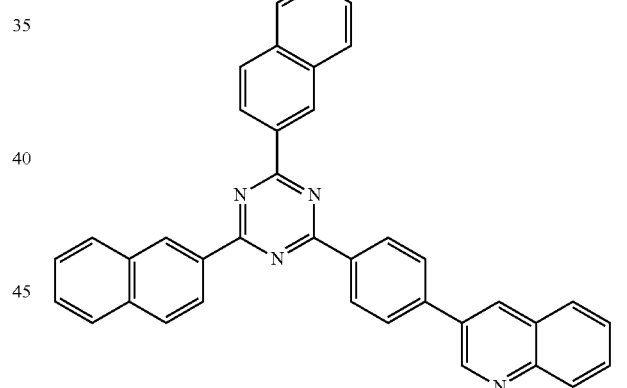
[Chemical Formula 12]

[Chemical Formula 13]
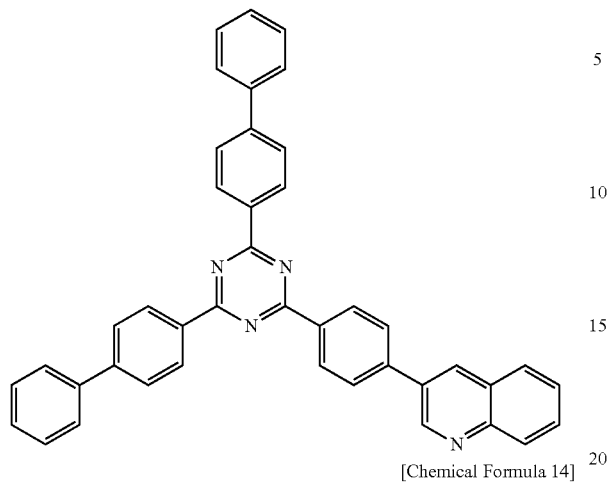
[Chemical Formula 14]
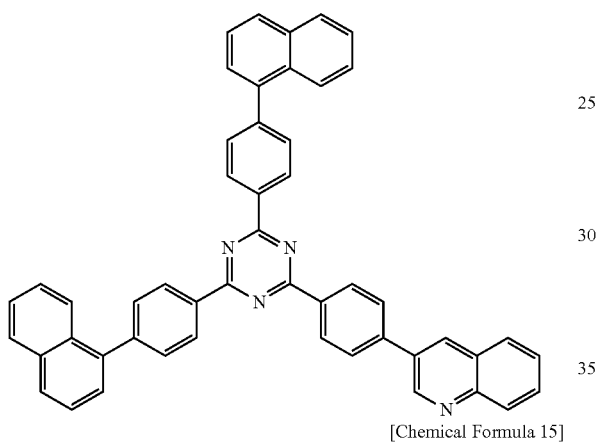
[Chemical Formula 15]
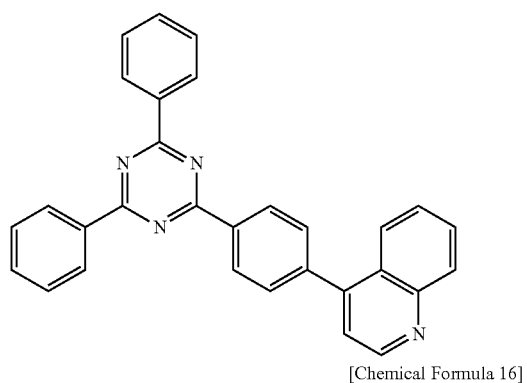
[Chemical Formula 16]
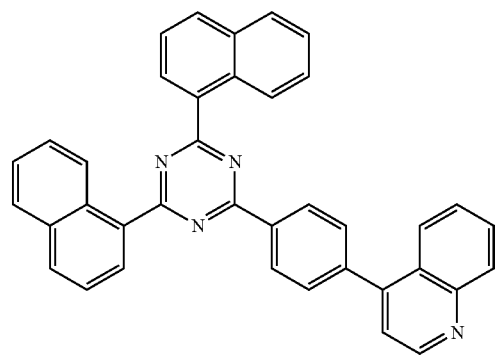
[Chemical Formula 17]
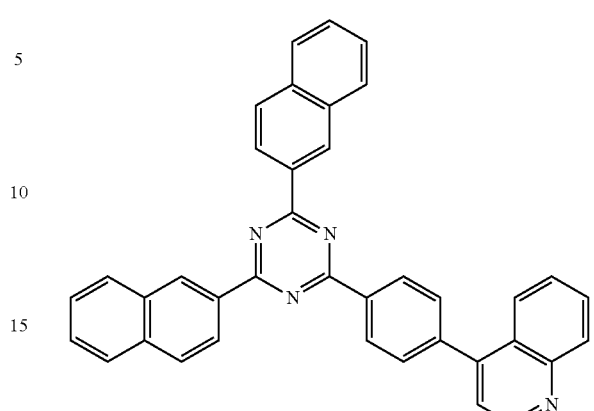
[Chemical Formula 18]
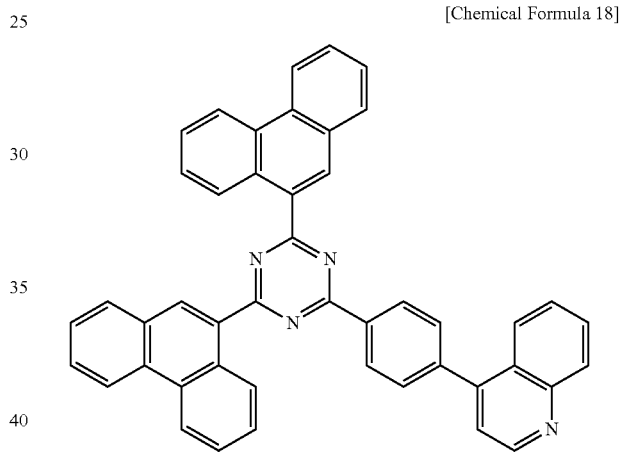
[Chemical Formula 19]
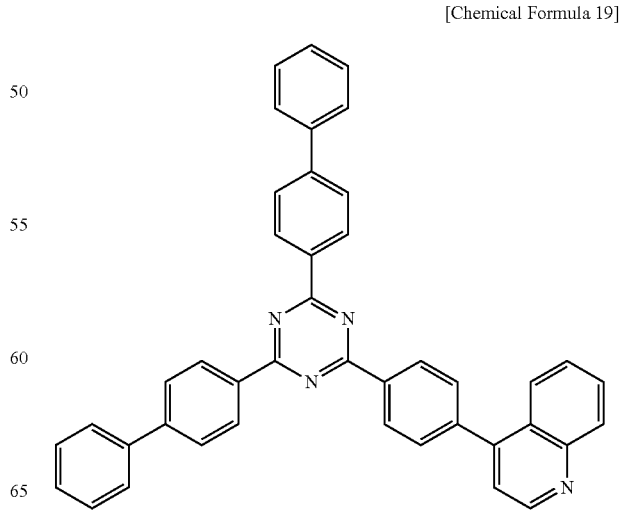

[Chemical Formula 20]
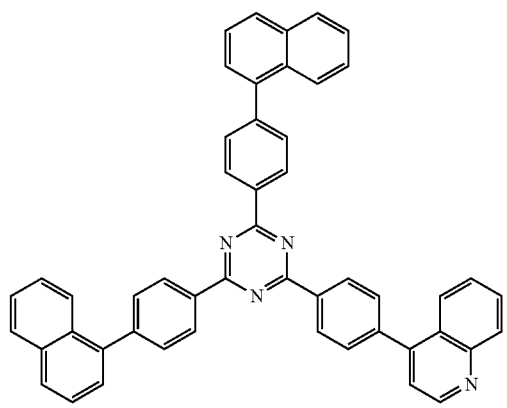
[Chemical Formula 21]
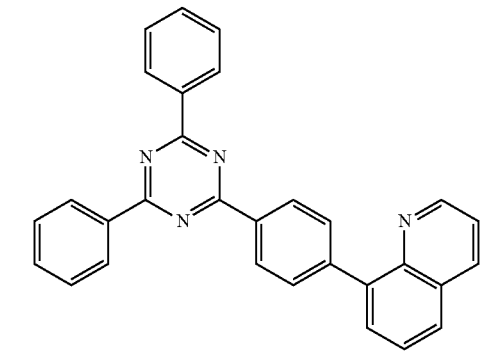
[Chemical Formula 22]
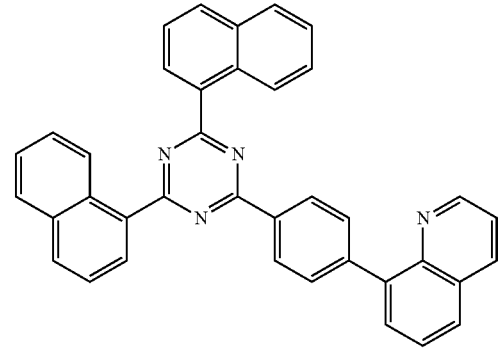
[Chemical Formula 23]
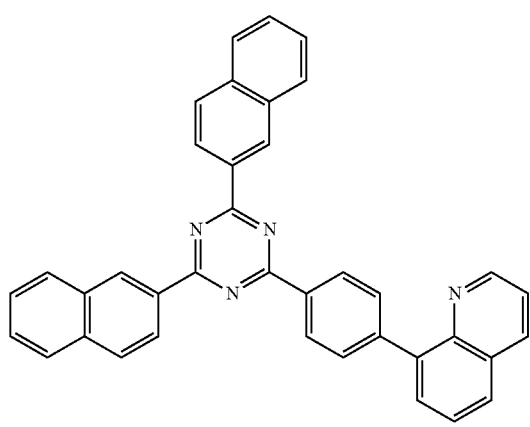
[Chemical Formula 24]
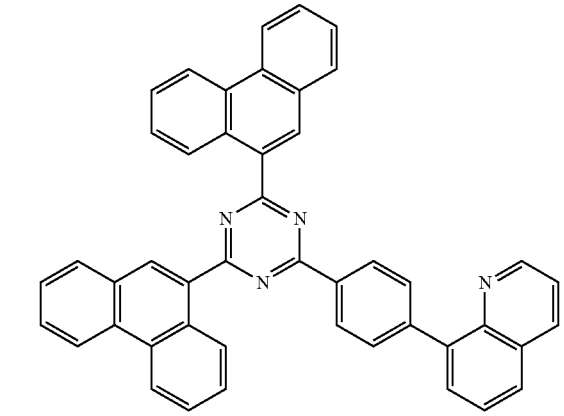
[Chemical Formula 25]
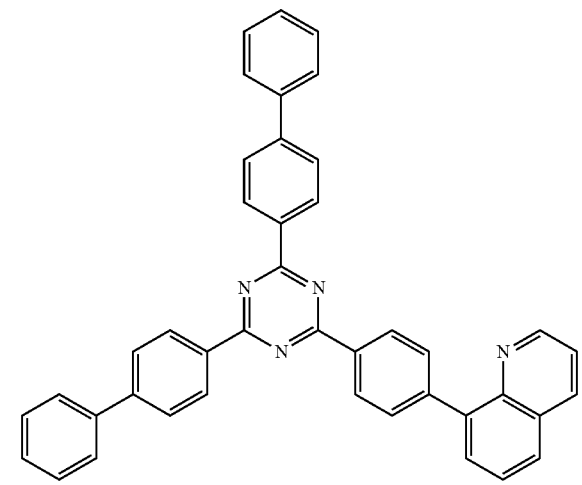
[Chemical Formula 26]
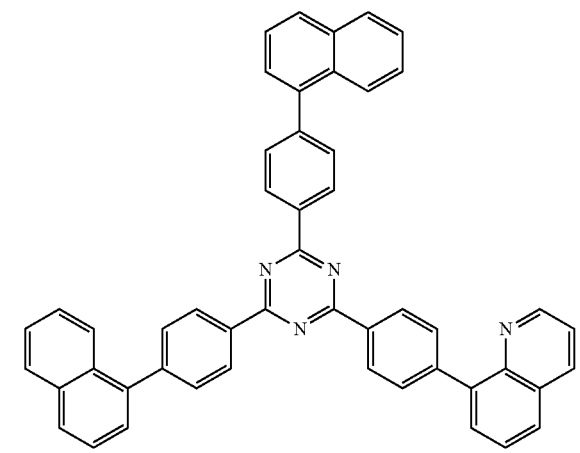

[Chemical Formula 27]
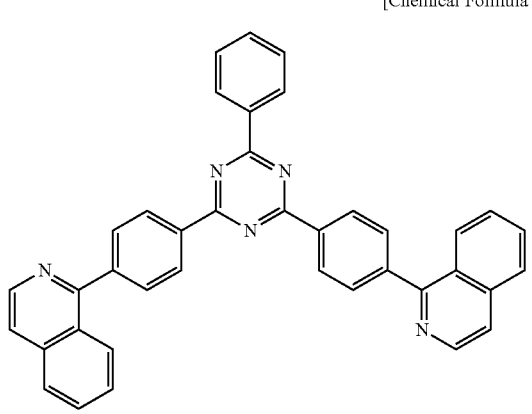
[Chemical Formula 28]
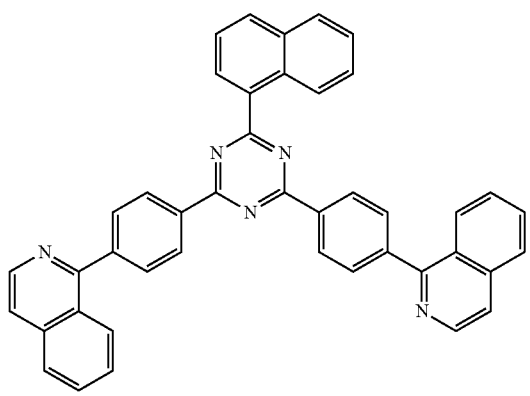
[Chemical Formula 29]
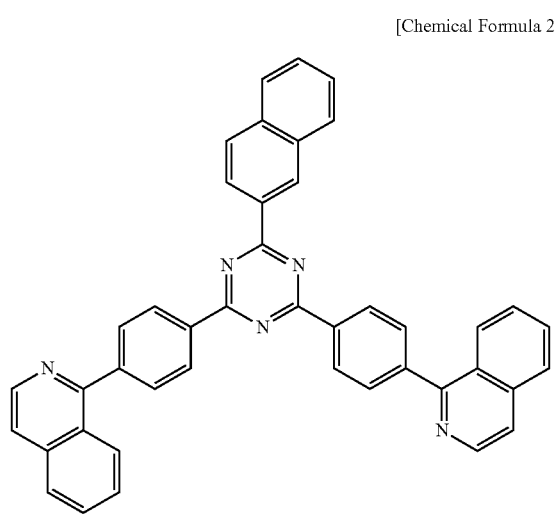
[Chemical Formula 30]
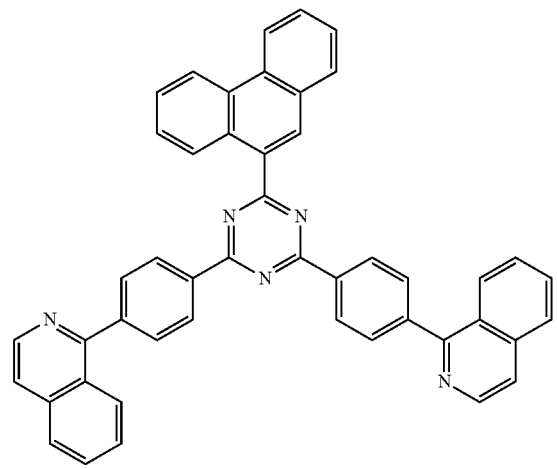
[Chemical Formula 31]
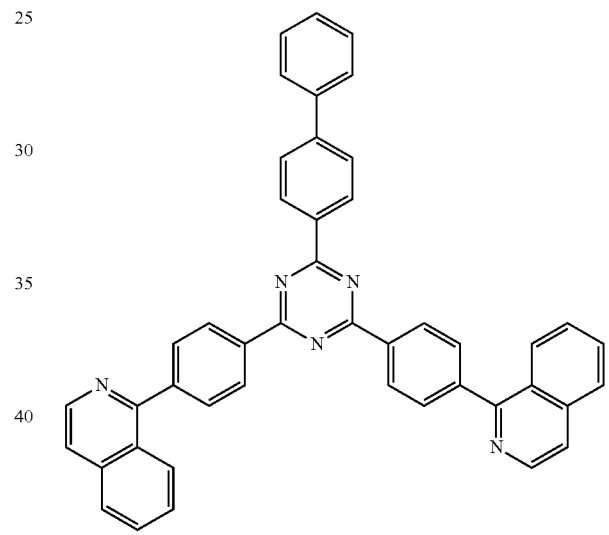
[Chemical Formula 32]
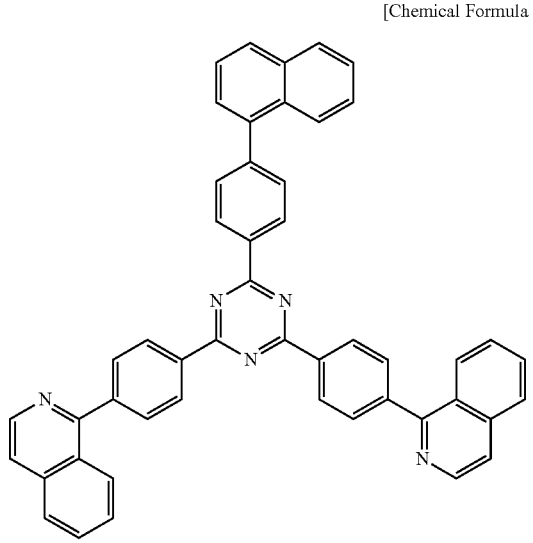

[Chemical Formula 33]
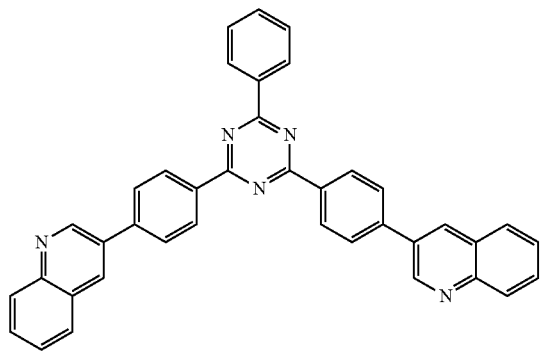
[Chemical Formula 34]
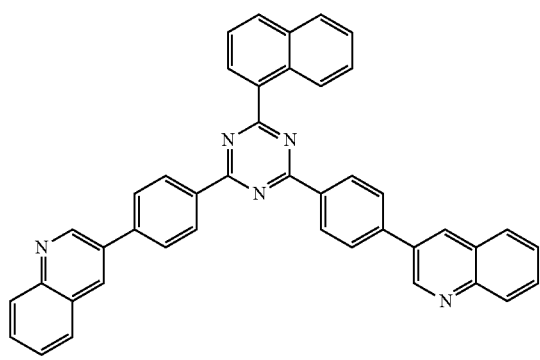
[Chemical Formula 35]
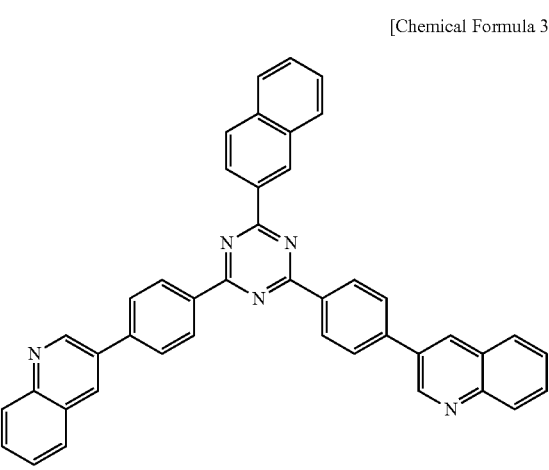
[Chemical Formula 36]
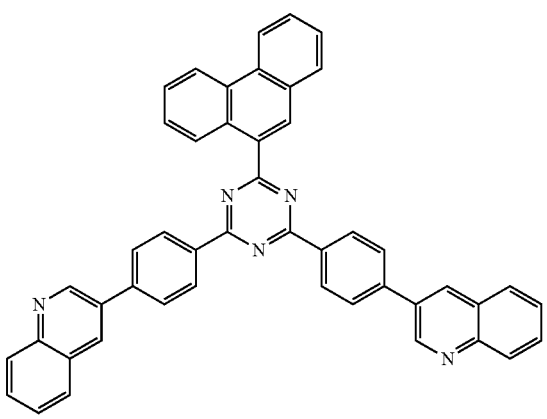
[Chemical Formula 37]
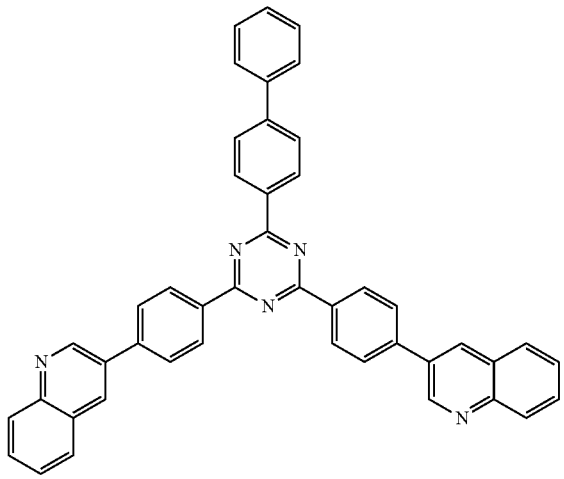
[Chemical Formula 38]
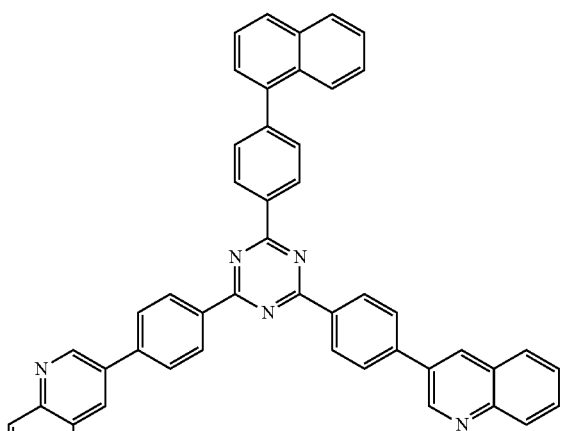
[Chemical Formula 39]

[Chemical Formula 40]
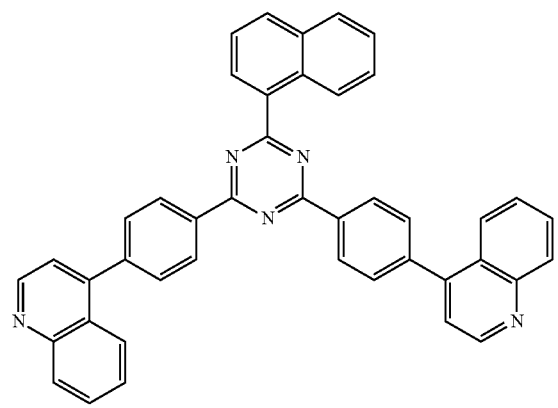
[Chemical Formula 41]
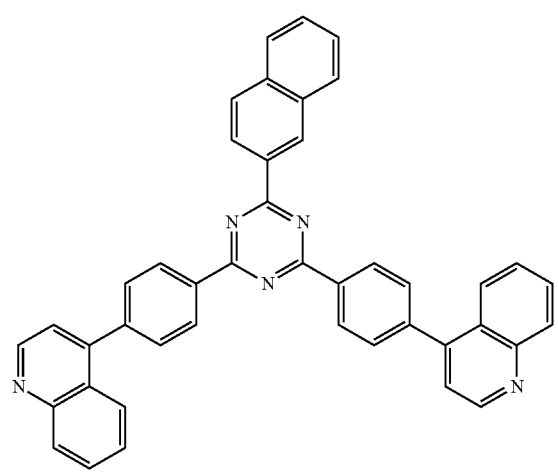
[Chemical Formula 42]
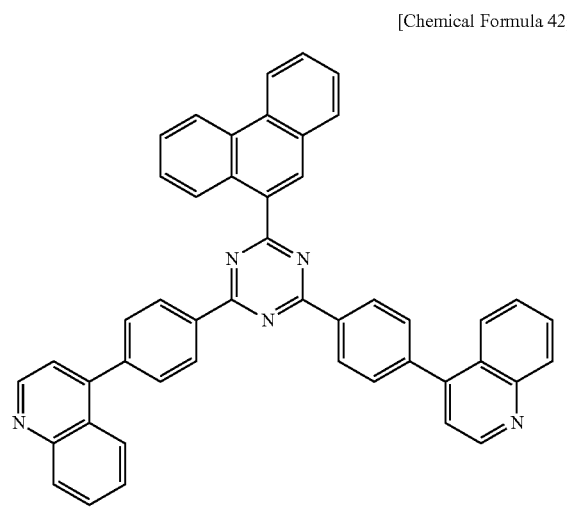
[Chemical Formula 43]
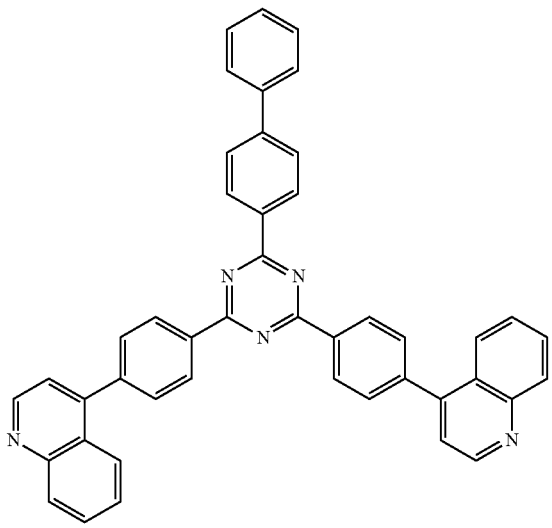
[Chemical Formula 44]
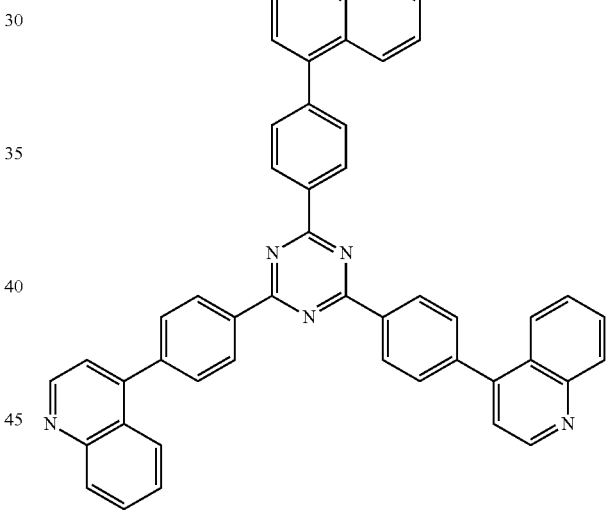
[Chemical Formula 45]
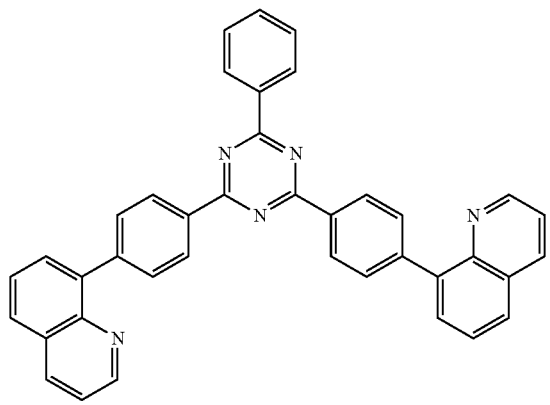

[Chemical Formula 46]

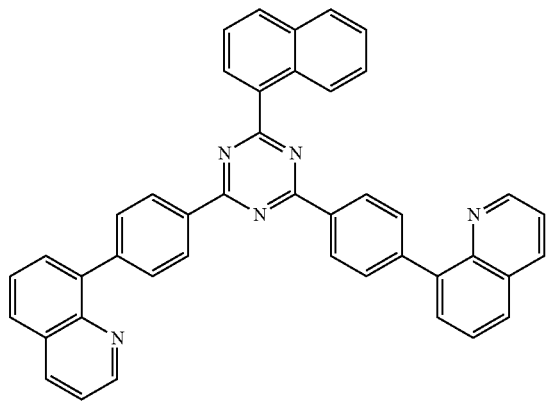

[Chemical Formula 47]

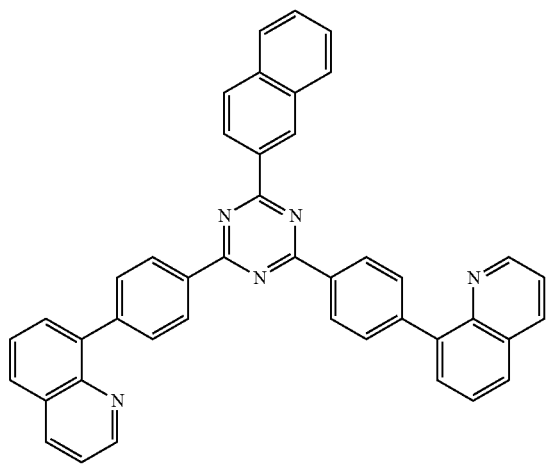

[Chemical Formula 48]

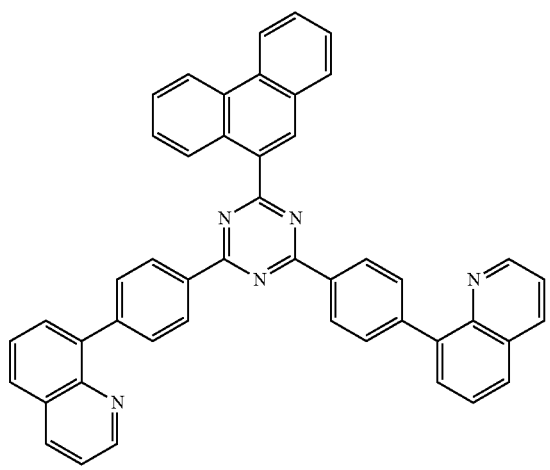

[Chemical Formula 49]

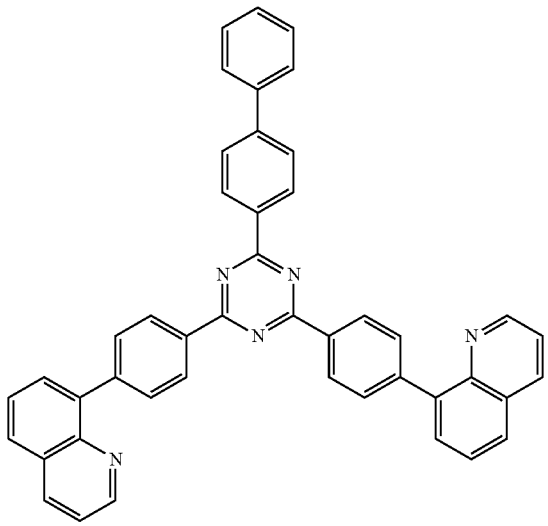

[Chemical Formula 50]

The compound of an embodiment may be included in a device that exhibits excellent life span characteristics due to molecular stability, even though they may have a low glass transition temperature (Tg).

The compound for an organic photoelectric device described above may play a role in emitting light or injecting, transporting electrons, and/or may act as a light emitting host together with a suitable dopant. For example, the compound for an organic photoelectric device may be used as a phosphorescent or fluorescent host material, a blue light emitting dopant material, or an electron transporting material.

The compound for an organic photoelectric device according to an embodiment may be used for an organic thin layer. For example, it may improve the life span characteristic, efficiency characteristic, electrochemical stability, and thermal stability of an organic photoelectric device, and may decrease a driving voltage.

Another embodiment provides an organic photoelectric device that includes the compound for an organic photoelectric device. The organic photoelectric device may include, e.g., an organic photoelectric device, an organic solar cell, an organic transistor, an organic photosensitive drum, an organic memory device, or the like. For example, the compound for an organic photoelectric device according to an embodiment may be included in an electrode or an electrode buffer layer in the organic solar cell to improve quantum efficiency, and/or it may be used as an electrode material for a gate, a source-drain electrode, or the like in the organic transistor.

Hereinafter, further details relating to the organic photoelectric device will be provided.

According to the present embodiment, the organic photoelectric device may include an anode, a cathode, and at least one organic thin layer interposed between the anode and the cathode. At least one organic thin layer may include the compound for an organic photoelectric device according to an embodiment.

The organic thin layer may include at least one of an emission layer, a hole transport layer (HTL), a hole injection layer (HIL), an electron transport layer (ETL), an electron injection layer (EIL), and a hole blocking film. At least one of the layers may include the compound for an organic photoelectric device according to an embodiment. For example, the electron transport layer (ETL) and/or the electron injection layer (EIL) may include the compound for an organic photoelectric device according to an embodiment. In addition, when the compound for an organic photoelectric device is included in the emission layer, the compound for an organic photoelectric device may be included as a phosphorescent or fluorescent host or as a fluorescent blue dopant material.

FIGS. 1 to 5 illustrate cross-sectional views showing an organic photoelectric device including the compound for an organic photoelectric device according to an embodiment.

Referring to FIGS. 1 to 5, organic photoelectric devices 100, 200, 300, 400, and 500 according to an embodiment may include at least one organic thin layer 105 interposed between an anode 120 and a cathode 110.

The anode 120 may include an anode material having a large work function to facilitate hole injection into an organic thin layer. The anode material may include: a metal, e.g., nickel, platinum, vanadium, chromium, copper, zinc, gold, or alloys thereof; a metal oxide, e.g., zinc oxide, indium oxide, indium tin oxide (ITO), or indium zinc oxide (IZO); a combined metal and oxide, e.g., ZnO:Al or $SnO_2$:Sb; or a conductive polymer, e.g., poly(3-methylthiophene), poly[3,4-(ethylene-1,2-dioxy)thiophene] (PEDT), polypyrrole, and polyaniline, but is not limited thereto. It is preferable to include a transparent electrode including indium tin oxide (ITO) as an anode.

The cathode 110 may include a cathode material having a small work function to facilitate electron injection into an organic thin layer. The cathode material may include, e.g., a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca, but is not limited thereto. It is preferable to include a metal electrode including aluminum as a cathode.

Referring to FIG. 1, the organic photoelectric device 100 may include an organic thin layer 105 including only an emission layer 130.

Figure 2:
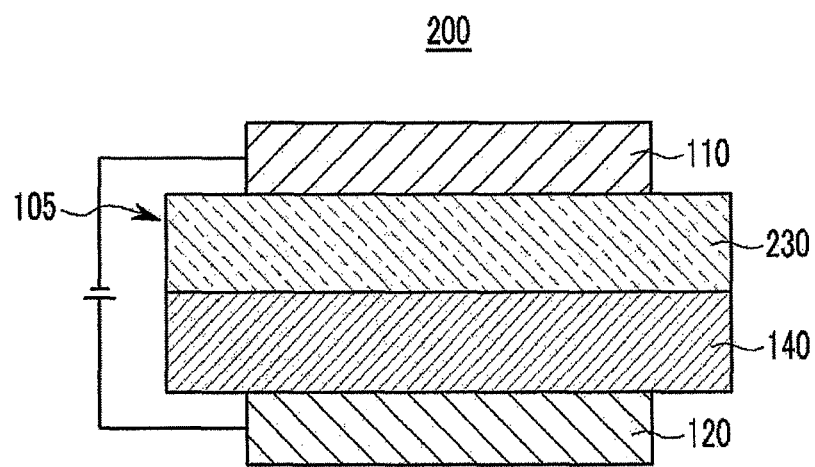

Referring to FIG. 2, the emission layer 230 may also function as an electron transport layer (ETL); and the hole transport layer (HTL) 140 layer may have an excellent binding property with a transparent electrode, e.g., ITO, and/or may exhibit excellent hole transporting properties.

Figure 3:
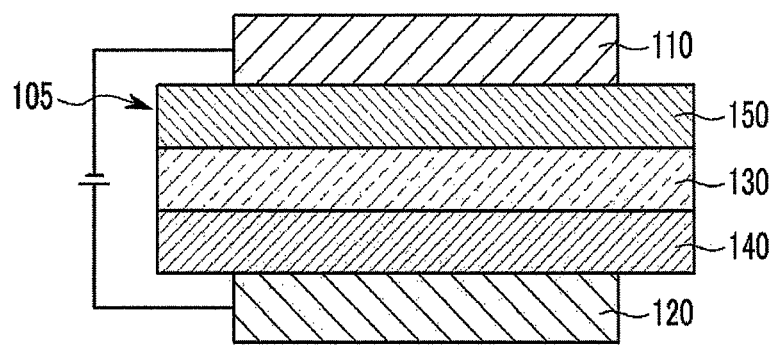

Referring to FIG. 3, a three-layered organic photoelectric device 300 may include an organic thin layer 105 including an electron transport layer (ETL) 150, an emission layer 130, and a hole transport layer (HTL) 140. The emission layer 130 may be independently installed, and layers having an excellent electron transporting property or an excellent hole transporting property may be separately stacked.

Figure 4:
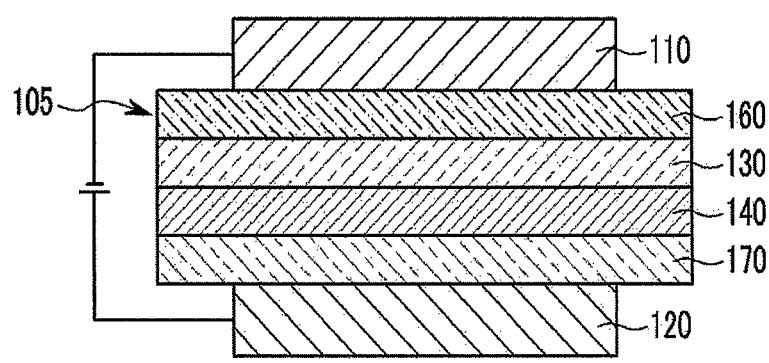

Referring to FIG. 4, a four-layered organic photoelectric device 400 may include an organic thin layer 105 including an electron injection layer (EIL) 160, an emission layer 130, a hole transport layer (HTL) 140, and a hole injection layer (HIL) 170 for binding with the anode formed of, e.g., ITO.

Figure 5:
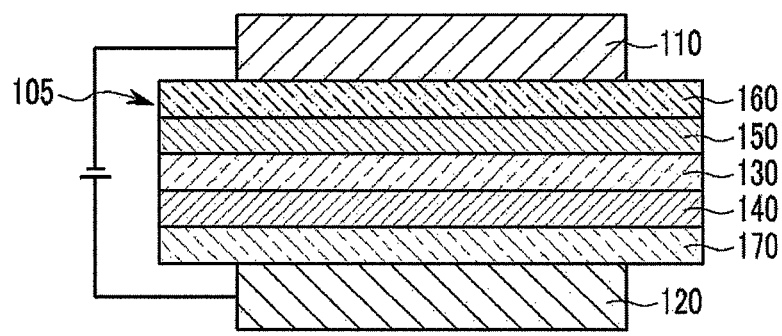

Referring to FIG. 5, a five-layered organic photoelectric device 500 may include an organic thin layer 105 including an electron transport layer (ETL) 150, an emission layer 130, a hole transport layer (HTL) 140, and a hole injection layer (HIL) 170, and may further include an electron injection layer (EIL) 160 to achieve a low voltage.

In FIGS. 1 to 5, the organic thin layer 105 including at least one of an electron transport layer (ETL) 150, an electron injection layer (EIL) 160, an emission layer 130 and 230, a hole transport layer (HTL) 140, a hole injection layer (HIL) 170, and combinations thereof, may include the compound for an organic photoelectric device according to an embodiment. The compound for the organic photoelectric device according to an embodiment may be included in, e.g., an electron transport layer (ETL) 150 or electron injection layer (EIL) 160. When it is used for the electron transport layer (ETL), it is possible to provide an organic photoelectric device having a simpler structure because it may not require an additional hole blocking layer (not shown).

Furthermore, when the compound for an organic photoelectric device according to an embodiment is included in the emission layer 130, the compound may be included as a phosphorescent or fluorescent host, or a fluorescent blue dopant.

The organic photoelectric device may be fabricated by, e.g., forming an anode on a substrate; forming an organic thin layer in accordance with a dry coating method such as evaporation, sputtering, plasma plating, and ion plating, or a wet coating method such as spin coating, dipping, and flow coating; and providing a cathode thereon.

Another embodiment provides a display device including the organic photoelectric device according to the above embodiment.

Hereinafter, embodiments are illustrated in more detail with reference to examples. However, the following are exemplary embodiments and are not limiting. For example, the following examples and experiments are given for illustrative purposes only and are not intended to limit the scope of this disclosure. Moreover, the Comparative Examples are set forth to highlight certain characteristics of certain embodiments, and are not to be construed as either limiting the scope of the invention as exemplified in the Examples or as necessarily always being outside the scope of the invention in every respect Preparation of Compound for Organic Photoelectric Device Example 1

Synthesis of Compound Represented by Chemical Formula 9

As an example of a compound for an organic photoelectric device according to an embodiment, the compound represented by Chemical Formula 9 was synthesized as in Reaction Scheme 1.

[Reaction Scheme 1]

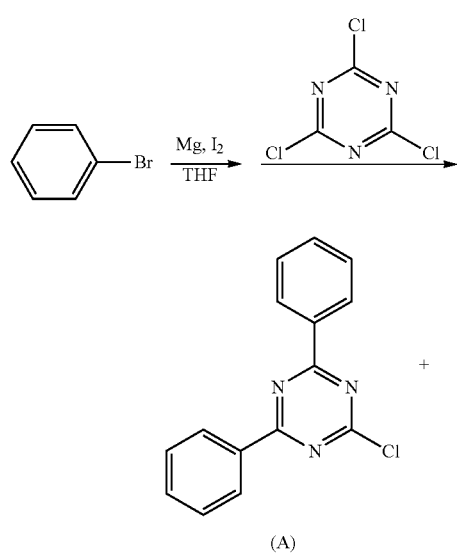

(A)

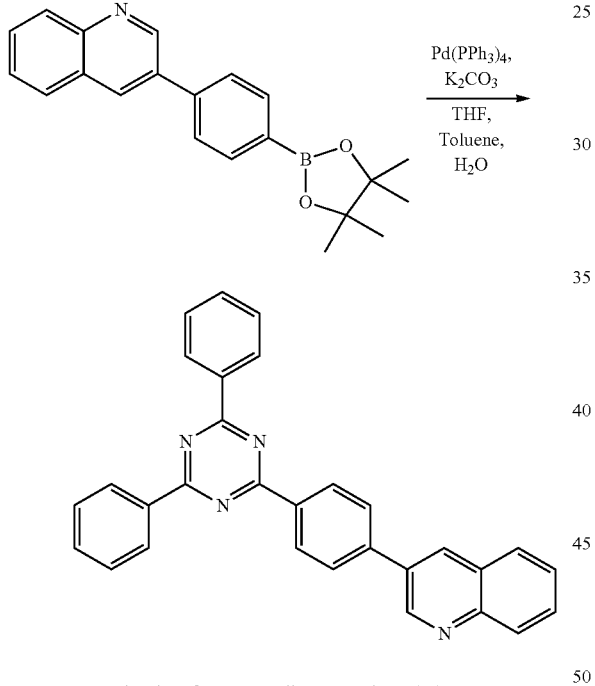

Step 1: Synthesis of Intermediate Product (A)

14.5 g (598 mmol) of magnesium and 3.0 g (12 mmol) of iodine were suspended in 50 ml of an anhydrous tetrahydrofuran solvent to prepare a suspension. A solution including 93.9 g (598 mmol) of bromobenzene diluted in 130 ml of anhydrous tetrahydrofuran was added to the suspension in a dropwise fashion for 30 minutes and the resulting mixture was refluxed for 2 hours while heating. The mixture was cooled to room temperature, and a solution including 36.7 g (199 mmol) of 1,3,5-trichlorotriazine that was dissolved in 130 ml of anhydrous tetrahydrofuran was added to the mixture in a dropwise fashion followed by agitating the mixture for 3 hours.

The organic solvent was removed by distillation under reduced pressure and then the residue was recrystallized with methanol to provide a crystal. The crystal was separated by filtration and washed with methanol to obtain 39.8 g (yield: 74.6%) of an intermediate product (A).

Step 2: Synthesis of Compound Represented by Chemical Formula 9

3.7 g (14 mmol) of the intermediate product (A) obtained in step 1, 5.0 g (15 mmol) of 3-(4-(4,4,5,5-tetramethyl-1,3,2-dioxaborolan-2-yl)phenyl)quinoline, and 0.39 g (0.3 mmol) of tetrakis(triphenylphosphine)palladium were suspended in a mixed solvent of 110 ml of tetrahydrofuran and 70 ml of toluene to prepare a suspension. 3.8 g (27 mmol) of potassium carbonate was dissolved in 70 ml of water to prepare a solution. The resulting solution was added to the suspension; and the mixture was refluxed for 24 hours while heating. After separating the reaction fluid into 2 layers, the organic layer was washed with a saturated sodium chloride aqueous solution and dried with anhydrous sodium sulfate.

The organic solvent was removed by distillation under reduced pressure, and then the residue was recrystallized with toluene to provide a crystal. The crystal was separated by filtration and washed with toluene to obtain 4.1 g (yield: 67.4%) of a compound Chemical Formula 9.

MS[M+1] 437.

Example 2

Synthesis of Compound Represented by Chemical Formula 11

As an example of a compound for an organic photoelectric device according to an embodiment, the compound represented by Chemical Formula 11 was synthesized as in Reaction Scheme 2.

[Reaction Scheme 2]

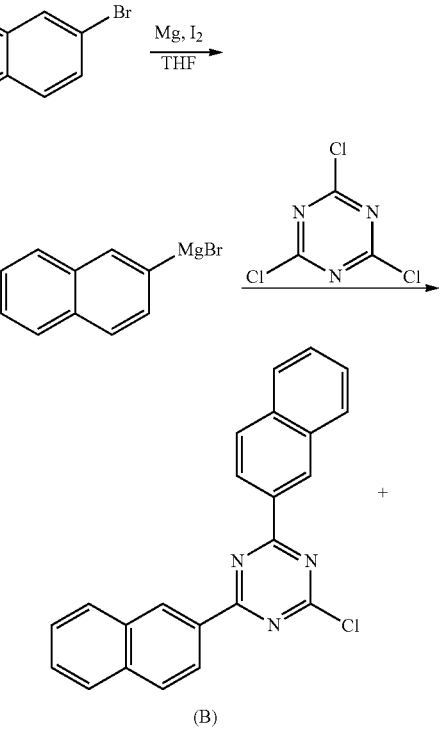

(B)

-continued

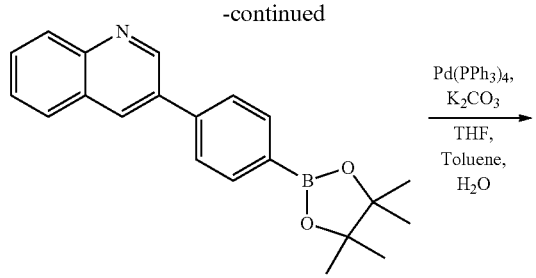

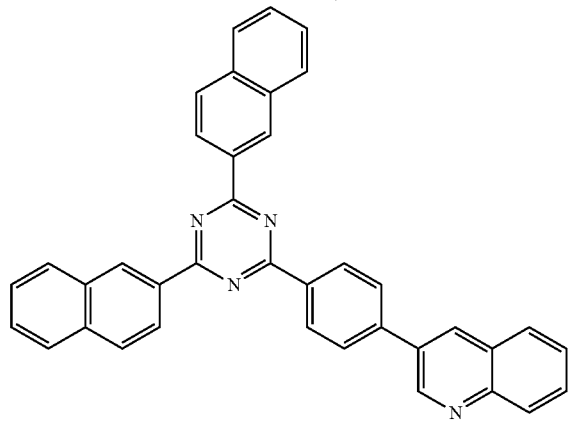

Step 1: Synthesis of Intermediate Product (B)

14.5 g (598 mmol) of magnesium and 3.0 g (12 mmol) of iodine were suspended in 50 ml of an anhydrous tetrahydrofuran solvent to prepare a suspension. A solution including 123.8 g (598 mmol) of bromonaphthalene diluted in 130 ml of anhydrous tetrahydrofuran was added to the suspension in a dropwise fashion for 30 minutes, and the resulting mixture was refluxed for 2 hours while heating. The mixture was cooled to room temperature, and a solution including 36.7 g (199 mmol) of 1,3,5-trichlorotriazine that was dissolved in 130 ml of anhydrous tetrahydrofuran was added to the mixture in a dropwise fashion followed by agitating the mixture for 3 hours.

The organic solvent was removed by distillation under reduced pressure, and then the residue was recrystallized with methanol to provide a crystal. The crystal was separated by filtration and washed with methanol to obtain 47.7 g (yield: 65.1%) of an intermediate product (B).

Step 2: Synthesis of Compound Represented by Chemical Formula 11

5.1 g (14 mmol) of the intermediate product (B) obtained in the step 1, 5.0 g (15 mmol) of (4-(4,4,5,5-tetramethyl-1,3,2-dioxaborolan-2-yl)phenyl)quinoline and 0.39 g (0.3 mmol) of tetrakis (triphenylphosphine)palladium were suspended in a mixed solvent of 150 ml of tetrahydrofuran and 100 ml of toluene to prepare a suspension. 3.8 g (27 mmol) of potassium carbonate was dissolved in 100 ml of water to prepare a solution. The resulting solution was added to the suspension, and the mixture was refluxed for 24 hours while heating. After separating the reaction fluid into 2 layers, the organic layer was washed with a saturated sodium chloride aqueous solution and dried with anhydrous sodium sulfate.

The organic solvent was removed by distillation under reduced pressure, and then the residue was recrystallized with toluene to provide a crystal. The crystal was separated by filtration and washed with toluene to obtain 5.4 g (yield: 71.8%) of a compound represented by Chemical Formula 11.
MS[M+1] 537.

Example 3

Synthesis of Compound Represented by Chemical Formula 23

As an example of a compound for an organic photoelectric device according to an embodiment, the compound represented by Chemical Formula 23 was synthesized as in Reaction Scheme 3.

[Reaction Scheme 3]

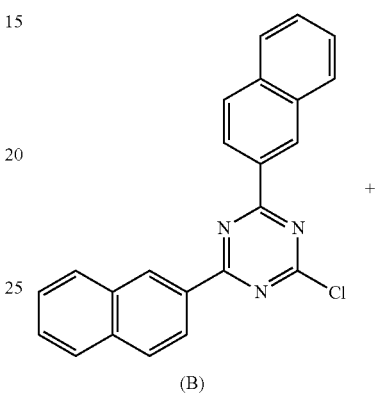

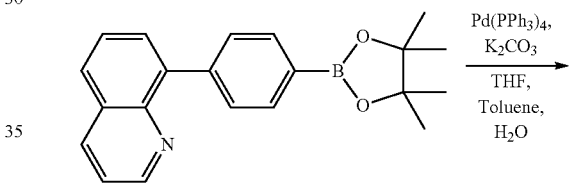

5.1 g (14 mmol) of the intermediate product (B) obtained in Example 2, 5.0 g (15 mmol) of 8-(4-(4,4,5,5-tetramethyl-1,3,2-dioxaborolan-2-yk)phenyl)quinoline, and 0.39 g (0.3 mmol) of tetrakis(triphenylphosphine)palladium were suspended in a mixed solvent of 15 0 ml of tetrahydrofuran and 100 ml of toluene to prepare a suspension. 3.8 g (27 mmol) of potassium carbonate was dissolved in 100 ml of water to prepare a solution. The resulting solution was added to the suspension, and the mixture was refluxed for 24 hours while heating. After separating the reaction fluid into 2 layers, the organic layer was washed with a saturated sodium chloride aqueous solution and dried with anhydrous sodium sulfate.

The organic solvent was removed by distillation under reduced pressure, and then the residue was recrystallized with toluene to provide a crystal. The crystal was separated by filtration and washed with toluene to obtain 4.9 g (yield: 65.4%) of a compound represented by Chemical Formula 23.

MS[M+1] 537.

Fabrication of Organic Photoelectric Device

Example 4

An ITO anode having a thickness of 1000 Å and an aluminum (Al) cathode having a thickness of 1000 Å were used.

The organic photoelectric device was fabricated by cutting an ITO glass substrate having sheet resistance of 15 Ω/cm² to a size of 50 mm×50 mm×0.7 mm, ultrasonic wave cleaning the same in acetone, isopropyl alcohol, and pure water for 5 minutes each, and UV ozone cleaning the same for 30 minutes to provide an anode.

$N^1,N^{1'}$-(biphenyl-4,4'-diyl)bis($N^1$-(naphthalen-2-yl)-$N^4$, $N^4$-diphenylbenzene-1,4-diamine) was deposited on the glass substrate to provide a hole injection layer (HIL) having a thickness of 65 nm; and N,N'-di(1-naphthyl)-N,N'-diphenylbenzidine (NPB) was deposited to provide a hole transport layer (HTL) having a thickness of 40 nm.

5 wt % of N,N,N',N'-tetrakis(3,4-dimethylphenyl)chrysene-6,12-diamine (fluorescent blue dopant) and 95 wt % of 9-(3-(naphthalen-1-yl)phenyl)-10-(naphthalen-2-yl)anthracene (fluorescent blue host) were deposited to provide an emission layer having a thickness of 25 nm.

Subsequently, the compound of Example 2 was deposited to provide an electron transport layer (ETL) having a thickness of 35 nm.

On the electron transport layer (ETL), Liq was vacuum-deposited to provide an electron injection layer (EIL) having a thickness of 0.5 nm, and Al was vacuum-deposited to provide a Liq/Al electrode having a thickness of 100 nm. The resulting organic photoelectric device had a structure shown in FIG. 5.

Example 5

An organic photoelectric device was fabricated in accordance with the same procedure as in Example 4, except that the compound of Example 3 was used to form the electron transport layer (ETL) instead of the compound of Example 2.

Comparative Example 1

An organic photoelectric device was fabricated in accordance with the same procedure as in Example 4, except that $Alq_3$ of the following Chemical Formula 51 to provide a 35 nm-thick electron transport layer (ETL) was used instead of the compound of Example 2.

[Chemical Formula 51]

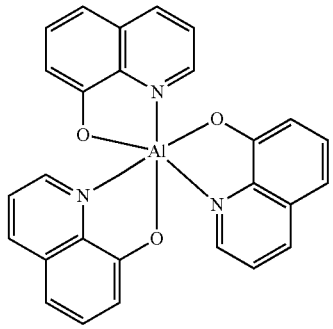

Measurement of Performance of Organic Photoelectric Device

Experimental Example

Measurement Method

Each of the obtained organic photoelectric devices was measured for luminance change, current density change depending upon the voltage, and Electric Power Efficiency. The specific method was as follows.

1) Measurement of Current Density Change Depending on Voltage Change

The obtained organic photoelectric device was measured for current value flowing in the unit device while increasing the voltage from 0 V to 14 V using a current-voltage meter (Keithley 2400), and the measured current value was divided by area to provide the result.

2) Measurement of Luminance Change Depending on Voltage Change

The obtained organic photoelectric device was measured for luminance using a luminance meter (Minolta Cs-1000A) while increasing the voltage from 0 V to 14V.

3) Measurement of Electric Power Efficiency

Current efficiency (cd/A) and electric power efficiency (lm/W) at the same luminance (1000 cd/m²) were calculated by using luminance and current density from 1) and 2) and voltage.

Table 1 shows results of the organic photoelectric devices according to Examples 4 and 5 as well as Comparative Example 1.

TABLE 1

| | Luminance (1000 cd/m²) | | | | |
|---|---|---|---|---|---|
| | Driving voltage | Current efficiency | Electric power efficiency | Color coordinate (CIE) | |
| | (V) | (cd/W) | (lm/W) | x | y |
| Ex. 4 | 6.2 | 8.51 | 4.33 | 0.15 | 0.15 |
| Ex. 5 | 5.7 | 7.98 | 4.40 | 0.15 | 0.15 |
| Comp. Ex. 1 | 7.3 | 6.84 | 2.94 | 0.15 | 0.23 |

Referring to Table 1, the organic photoelectric devices according to Examples 4 and 5, e.g., devices including the compounds for an electron transport layer (ETL), exhibited a low driving voltage as well as excellent performance of high efficiency, compared with the organic photoelectric device according to Comparative Example 1, which included $Alq_3$ for an electron transport layer (ETL).

By way of summation and review, an organic photoelectric device may include, e.g., an organic light emitting diode (OLED), an organic solar cell, an organic photo-conductor drum, an organic transistor, an organic memory device, etc., and may include a hole injecting or transporting material, an electron injecting or transporting material, or a light emitting material.

For example, the organic light emitting diode (OLED) has recently drawn attention due to an increase in demand for flat panel displays. In general, organic light emission refers to transformation of electrical energy to photo-energy.

The organic light emitting diode may transform electrical energy into light by applying current to an organic light emitting material. The organic light emitting diode may have a structure in which a functional organic material layer is interposed between an anode and a cathode. The organic material layer may include a multi-layer including different materials, e.g., a hole injection layer (HIL), a hole transport layer (HTL), an emission layer, an electron transport layer (ETL), and an electron injection layer (EIL), in order to improve efficiency and stability of an organic light emitting diode.

In such an organic light emitting diode, when a voltage is applied between an anode and a cathode, holes from the anode and electrons from the cathode may be injected to an organic material layer. The generated excitons may generate light having certain wavelengths when returning to a ground state.

A phosphorescent material may emit light by transiting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer may include a light emitting material and a charge transport material, e.g., a hole injection material, a hole transport material, an electron transport material, an electron injection material, and so on.

The light emitting material may be classified as blue, green, and red light emitting materials according to emitted colors. Yellow and orange light emitting materials may emit colors approaching natural colors.

When one material is used as a light emitting material, a maximum light emitting wavelength may be shifted to a long wavelength or color purity may decrease due to interactions between molecules. Also, device efficiency may decrease because of a light emitting quenching effect. Therefore, a host/dopant system may be included as a light emitting material in order to improve color purity and increase luminous efficiency and stability through energy transfer.

In order to implement excellent performance of an organic light emitting diode, a material included in an organic material layer, e.g., a hole injection material, a hole transport material, a light emitting material, an electron transport material, an electron injection material, and a light emitting material such as a host and/or a dopant, should be stable and have good efficiency. The compound of an embodiment may be used for other organic photoelectric devices.

The compound for an organic photoelectric device according to an embodiment may exhibit high thermal stability. Also, the compound may improve the life span of organic photoelectric devices from the performance results of organic photoelectric devices indicating a low driving voltage and high luminous efficiency.

The compound including a triazine core with which a quinolinyl group or an isoquinolinyl group is combined may have a high electron transfer capability and hole inhibition capability and thus may have a merit in terms of efficiency and driving voltage. Also, the compound may exhibit enhanced electrochemical and thermal stability due to the triazine core structure combining with an aryl group. It is expected that these structures may improve the life span of a device.

Thus, the embodiments provide a compound for an organic photoelectric device capable of providing an organic photoelectric device having good life span, efficiency, electrochemical stability, and thermal stability.

The embodiments also provide a compound for an organic photoelectric device that may act as a hole injection, hole transport, light emitting, or electron injection and/or transport material, and may also act as a light emitting host along with an appropriate dopant.

The embodiments also provide an organic photoelectric device having excellent life span, efficiency, driving voltage, electrochemical stability, and thermal stability.

The embodiments also provide a display device including the organic photoelectric device.

The embodiments also provide a compound exhibiting excellent electrochemical and thermal stability.

The embodiments also provide an organic photoelectric device having an excellent life span and high luminous efficiency at a low driving voltage.

Exemplary embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A compound for an organic photoelectric device represented by the following Chemical Formula 1:

[Chemical Formula 1]

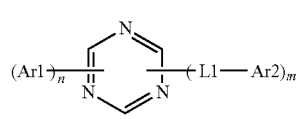

wherein, in Chemical Formula 1,
Ar1 is an unsubstituted C10 to C30 fused aryl group or a substituted C10 to C30 fused aryl group substituted with a C1 to C30 alkyl group, a C1 to C10 alkylsilyl group, a C3 to C30 cycloalkyl group, a C6 to C30 aryl group, a C1 to C10 alkoxy group, a fluoro group, a C1 to C10 trifluoroalkyl group, or a cyano group,
Ar2 is a substituted or unsubstituted quinolinyl group or a substituted or unsubstituted isoquinolinyl group,
L1 is a substituted or unsubstituted C6 to C20 arylene group, and
n and m are integers of 1 or 2, m+n being 3.

2. The compound for an organic photoelectric device as claimed in claim 1, wherein Ar1 is selected from a substituted or unsubstituted naphthyl group, a substituted or unsubstituted naphthylphenyl group, a substituted or unsubstituted phenanthrenyl group, a substituted or unsubstituted anthracenyl group, and a substituted or unsubstituted pyrenyl group.

3. The compound for an organic photoelectric device as claimed in claim 1, wherein Ar2 is a substituted or unsubstituted quinolinyl group.

4. The compound for an organic photoelectric device as claimed in claim 3, wherein L1 is linked to Ar2 at a number 4 or 8 position of the substituted or unsubstituted quinolinyl group thereof.

5. The compound for an organic photoelectric device as claimed in claim 1, wherein L1 is selected from a substituted or unsubstituted phenylene, a substituted or unsubstituted biphenylene, and a substituted or unsubstituted naphthylene.

6. An organic photoelectric device, comprising:
an anode;
a cathode, and
one or more organic thin layers between the anode and cathode,
wherein at least one of the organic thin layers includes the compound for an organic photoelectric device as claimed in claim 1.

7. The organic photoelectric device as claimed in claim 6, wherein the one or more organic thin layers includes at least one of an emission layer, a hole transport layer (HTL), a hole injection layer (HIL), an electron transport layer (ETL), an electron injection layer (EIL), and a hole blocking layer.

8. The organic photoelectric device as claimed in claim 6, wherein the at least one organic thin layer includes at least one of an electron transport layer (ETL) and an electron injection layer (EIL), the compound for the organic photoelectric device being included in the electron transport layer (ETL) or the electron injection layer (EIL).

9. The organic photoelectric device as claimed in claim 6, wherein the at least one organic thin layer includes an emission layer, the compound for the organic photoelectric device being included in the emission layer.

10. The organic photoelectric device as claimed in claim 6, wherein the at least one organic thin layer includes an emission layer, the compound for the organic photoelectric device being a phosphorescent or fluorescent host material in the emission layer.

11. The organic photoelectric device as claimed in claim 6, wherein the at least one organic thin layer includes an emission layer, the compound for the organic photoelectric device being a fluorescent blue dopant material in the emission layer.

12. The organic photoelectric device as claimed in claim 6, wherein the organic photoelectric device is an organic light emitting device, an organic solar cell, an organic transistor, an organic photo-conductor drum, or an organic memory device.

* * * * *